(12) United States Patent
Yusibov et al.

(10) Patent No.: US 7,692,063 B2
(45) Date of Patent: Apr. 6, 2010

(54) PRODUCTION OF FOREIGN NUCLEIC ACIDS AND POLYPEPTIDES IN SPROUT SYSTEMS

(75) Inventors: Vidadi Yusibov, Havertown, PA (US); Vadim Mett, Newark, DE (US); Shailaja Rabindran, Newark, DE (US); Moneim Shamloul, Newark, DE (US); Burt Ensley, Sedona, AZ (US)

(73) Assignees: iBio, Inc., Newark, DE (US); Fraunhofer USA, Inc., Newark, DE (US)

( * ) Notice: Subject to any disclaimer, the term of this patent is extended or adjusted under 35 U.S.C. 154(b) by 39 days.

(21) Appl. No.: 11/353,905

(22) Filed: Feb. 13, 2006

(65) Prior Publication Data

US 2006/0277634 A1    Dec. 7, 2006

Related U.S. Application Data

(63) Continuation-in-part of application No. 10/770,600, filed on Feb. 3, 2004, now Pat. No. 7,491,509, and a continuation-in-part of application No. 10/294,314, filed on Nov. 12, 2002.

(60) Provisional application No. 60/652,186, filed on Feb. 11, 2005, provisional application No. 60/444,615, filed on Feb. 3, 2003.

(51) Int. Cl.
    *C12N 15/82*    (2006.01)
(52) U.S. Cl. ........................ 800/294; 800/288; 435/69.1
(58) Field of Classification Search ........................ None
    See application file for complete search history.

(56) References Cited

U.S. PATENT DOCUMENTS

| | | | |
|---|---|---|---|
| 3,747,501 A | 7/1973 | Honda et al | |
| 4,028,847 A | 6/1977 | Davis et al. | |
| 4,196,265 A | 4/1980 | Koprowski et al. | |
| 4,683,202 A | 7/1987 | Mullis | |
| 4,816,567 A | 3/1989 | Cabitl et al. | |
| 4,935,496 A | 6/1990 | Kudo et al. | |
| 4,956,282 A | 9/1990 | Goodman et al. | |
| 5,175,102 A | 12/1992 | Baulcombe et al. | |
| 5,223,409 A | 6/1993 | Ladner et al. | |
| 5,316,931 A | 5/1994 | Donson et al. | |
| 5,403,484 A | 4/1995 | Ladner et al. | |
| 5,427,908 A | 6/1995 | Dower et al. | |
| 5,447,858 A | 9/1995 | Key et al. | |
| 5,464,763 A | 11/1995 | Schilperoort et al. | |
| 5,491,076 A | 2/1996 | Carrington et al. | |
| 5,500,360 A | 3/1996 | Ahlquist et al. | |
| 5,502,167 A | 3/1996 | Waldmann et al. | |
| 5,530,101 A | 6/1996 | Queen et al. | |
| 5,545,806 A | 8/1996 | Lonberg et al. | |
| 5,545,807 A | 8/1996 | Surani et al. | |
| 5,558,864 A | 9/1996 | Bendig et al. | |
| 5,565,332 A | 10/1996 | Hoogenboom et al. | |
| 5,565,347 A | 10/1996 | Fillatti et al. | |
| 5,569,825 A | 10/1996 | Lonber et al. | |
| 5,580,717 A | 12/1996 | Dower et al. | |
| 5,585,089 A | 12/1996 | Queen et al. | |
| 5,589,367 A | 12/1996 | Donson et al. | |
| 5,602,242 A | 2/1997 | Ahlquist et al. | |
| 5,625,126 A | 4/1997 | Lonber et al. | |
| 5,627,060 A | 5/1997 | Ahlquist et al. | |
| 5,633,425 A | 5/1997 | Lonber et al. | |
| 5,639,641 A | 6/1997 | Pedersen et al. | |
| 5,654,184 A | 8/1997 | Curtiss, III et al. | |
| 5,658,727 A | 8/1997 | Barbas et al. | |
| 5,661,016 A | 8/1997 | Lonberg et al. | |
| 5,667,988 A | 9/1997 | Barbas et al. | |
| 5,679,880 A | 10/1997 | Curtiss, III et al. | |
| 5,686,079 A | 11/1997 | Curtiss, III et al. | |
| 5,693,493 A | 12/1997 | Robinson et al. | |
| 5,693,761 A | 12/1997 | Queen et al. | |
| 5,693,762 A | 12/1997 | Queen et al. | |
| 5,698,417 A | 12/1997 | Robinson et al. | |
| 5,698,426 A | 12/1997 | Huse | |
| 5,702,892 A | 12/1997 | Mulligan-Kehoe | |
| 5,705,154 A | 1/1998 | Dalie et al. | |
| 5,728,300 A | 3/1998 | Kapulnik et al. | |

(Continued)

FOREIGN PATENT DOCUMENTS

AU         721534         4/1998

(Continued)

OTHER PUBLICATIONS

Porta C. et al. Use of viral replicons for the expression of genes in plants. Mol Biotechnol. Jun. 1996;5(3);209-21.*

(Continued)

*Primary Examiner*—Cynthia Collins
(74) *Attorney, Agent, or Firm*—Fish & Richardson P.C.

(57) ABSTRACT

The present invention provides systems and methods for producing a nucleic acid or protein in transgenic sprouted seedlings or sprouted seedlings engineered to transiently express a nucleic acid or protein of interest. The sprouted seedlings of the invention are grown in a contained, regulatable environment, wherein expression of a pharmaceutically active protein is controlled by an exogenously inducible promoter or a viral promoter. The sprouted seedlings may be eaten live or preferably harvested live to preserve the maximal biological activity of the nucleic acid or protein.

10 Claims, 9 Drawing Sheets

U.S. PATENT DOCUMENTS

| | | | |
|---|---|---|---|
| 5,733,743 A | 3/1998 | Johnson et al. | |
| 5,750,078 A | 5/1998 | Shitara et al. | |
| 5,750,871 A | 5/1998 | Moloney et al. | |
| 5,759,817 A | 6/1998 | Barbas | |
| 5,766,885 A | 6/1998 | Carrington et al. | |
| 5,770,403 A | 6/1998 | Dalie et al. | |
| 5,770,429 A | 6/1998 | Lonber et al. | |
| 5,811,653 A | 9/1998 | Turpen | |
| 5,846,795 A | 12/1998 | Ahlquist et al. | |
| 5,853,576 A | 12/1998 | Kapulnik et al. | |
| 5,855,866 A | 1/1999 | Thorpe et al. | |
| 5,866,785 A | 2/1999 | Ronson et al. | |
| 5,874,087 A | 2/1999 | Lomonossoff et al. | |
| 5,877,289 A | 3/1999 | Thorpe et al. | |
| 5,888,789 A | 3/1999 | Rodriguez et al. | |
| 5,889,189 A | 3/1999 | Rodriguez et al. | |
| 5,889,190 A | 3/1999 | Ronson et al. | |
| 5,889,191 A | 3/1999 | Turpen | |
| 5,917,117 A | 6/1999 | Ensle et al. | |
| 5,922,602 A | 7/1999 | Kumagai et al. | |
| 5,939,541 A | 8/1999 | Vance et al. | |
| 5,965,132 A | 10/1999 | Thorpe et al. | |
| 5,965,794 A | 10/1999 | Turpen | |
| 5,994,628 A * | 11/1999 | Rodriguez | 800/298 |
| 6,004,555 A | 12/1999 | Thorpe et al. | |
| 6,015,692 A | 1/2000 | Gyuris et al. | |
| 6,042,832 A | 3/2000 | Koprowski et al. | |
| 6,051,239 A | 4/2000 | Simpson et al. | |
| 6,054,566 A | 4/2000 | Donson et al. | |
| 6,077,992 A | 6/2000 | Yadav | |
| 6,093,399 A | 7/2000 | Thorpe et al. | |
| 6,127,145 A | 10/2000 | Sutliff et al. | |
| 6,261,535 B1 | 7/2001 | Thorpe et al. | |
| 6,297,357 B1 | 10/2001 | Giordano | |
| 6,331,415 B1 | 12/2001 | Cabilly et al. | |
| 6,369,296 B1 | 4/2002 | Ratcliff et al. | |
| 6,376,752 B1 | 4/2002 | Kumagai et al. | |
| 6,395,962 B1 | 5/2002 | Vance | |
| 6,399,317 B1 | 6/2002 | Weimer | |
| 6,410,317 B1 | 6/2002 | Farmer | |
| 6,448,070 B1 | 9/2002 | Koprowski et al. | |
| 6,500,644 B1 | 12/2002 | Borchert et al. | |
| 6,531,647 B1 | 3/2003 | Baulcombe et al. | |
| 6,596,698 B1 | 7/2003 | Giordano et al. | |
| 6,632,980 B1 | 10/2003 | Yadav et al. | |
| 6,635,805 B1 | 10/2003 | Baulcombe et al. | |
| 6,660,500 B2 | 12/2003 | Turpen et al. | |
| 6,740,740 B2 | 5/2004 | Garger et al. | |
| 6,841,659 B2 | 1/2005 | Turpen et al. | |
| 6,852,319 B2 | 2/2005 | Hein et al. | |
| 6,858,426 B1 | 2/2005 | Zhu et al. | |
| 7,012,172 B2 | 3/2006 | Yusibov | |
| 2003/0097678 A1 | 5/2003 | Kushinov et al. | |
| 2003/0135882 A1 | 7/2003 | Metzlaff et al. | |
| 2003/0211568 A1 | 11/2003 | Ashkenazi et al. | |
| 2004/0019930 A1 | 1/2004 | Yusibov | |
| 2004/0043886 A1 | 3/2004 | Akada et al. | |
| 2004/0088757 A1 | 5/2004 | Roberts et al. | |
| 2004/0092470 A1 | 5/2004 | Leonard et al. | |
| 2004/0093643 A1 | 5/2004 | Ensle | |
| 2005/0026291 A1 | 2/2005 | Fedorkin et al. | |
| 2005/0091706 A1 | 4/2005 | Klimyuk et al. | |
| 2005/0114920 A1 | 5/2005 | Yusibov et al. | |
| 2006/0085871 A1 | 4/2006 | Yusibov et al. | |
| 2006/0265787 A1 | 11/2006 | Piruzian et al. | |
| 2006/0277634 A1 | 12/2006 | Yusibov et al. | |
| 2007/0178148 A1 | 8/2007 | Yusibov et al. | |
| 2007/0292862 A1 | 12/2007 | Baulcombe et al. | |
| 2007/0300330 A1 | 12/2007 | Marillonnet et al. | |
| 2008/0241931 A1 | 10/2008 | Fedorkin et al. | |

FOREIGN PATENT DOCUMENTS

| | | |
|---|---|---|
| EP | 0067553 | 12/1982 |
| WO | WO8908145 | 9/1989 |
| WO | WO9311161 | 6/1993 |
| WO | WO9321334 | 10/1993 |
| WO | WO9420135 | 9/1994 |
| WO | WO9514099 | 5/1995 |
| WO | WO9602555 | 2/1996 |
| WO | WO9612028 | 4/1996 |
| WO | WO9627673 | 9/1996 |
| WO | WO9636701 | 11/1996 |
| WO | WO9640229 | 12/1996 |
| WO | WO9713864 | 4/1997 |
| WO | WO9738095 | 10/1997 |
| WO | WO9808375 | 3/1998 |
| WO | WO9814595 | 4/1998 |
| WO | WO9845331 | 10/1998 |
| WO | WO0020612 | 4/2000 |
| WO | WO0023593 | 4/2000 |
| WO | WO0025574 | 5/2000 |
| WO | WO0046350 | 8/2000 |
| WO | WO0138512 | 5/2001 |
| WO | WO0141559 | 6/2001 |
| WO | WO0268664 | 9/2002 |
| WO | WO200411614 | 2/2004 |
| WO | WO200443886 | 5/2004 |
| WO | WO200444161 | 5/2004 |
| WO | WO200470016 | 8/2004 |
| WO | WO200526375 | 3/2005 |
| WO | WO200549839 | 6/2005 |
| WO | WO200581905 | 9/2005 |
| WO | WO200795304 | 8/2007 |
| WO | WO2007117264 | 10/2007 |
| WO | WO2007135480 | 11/2007 |
| WO | WO2007137788 | 12/2007 |

OTHER PUBLICATIONS

Fischer R. et al. Molecular farming of pharmaceutical proteins. Transgenic Res. 2000;9(4-5):279-99.*

Parmenter D.L. Production of biologically active hirudin in plant seeds using oleosin partitioning. Plant Mol Biol. Dec. 1995;29(6):1167-80.*

Grimsley N. et al. "Agroinfection," an alternative route for viral infection of plants by using the Ti plasmid. Proc Natl Acad Sci U S A. May 1986;83(10):3282-3286.*

Li Y. et al. Expression of a human lactoferrin N-lobe in *Nicotiana benthmiana* with potato virus X-based agroinfection. Biotechnol Lett. Jun. 2004;26(12):953-7.*

U.S. Appl. No. 10/558,109, Yusibov et al.

U.S. Appl. No. 11/498,522, Mett et al.

Altschul et al., (1997), *Nucleic Acids Res.*, 25:3389-3402.

Altschul et al., (1990), *J. Mol. Biol.*, 215:403-410.

An et al., (1985), *EMBO J.*, 4:277-284.

Angell et al., *EMBO J.*, 1997, 6(12):3675-3684.

Arakawa et al., "A Plant-Based Cholera Toxin B Subunit-Insulin Fusion Protein Protects Against The Development of Autoimmune Diabetes" *Nat. Biotechnol.* 1998, 16: 934-936.

Ay et al., (1998), *Proteins*, 30(2):155-67.

Barfield et al., "Gene Transfer in Plants of *Brassica Juncea* Using Agrobacterium Tumefaciens Mediated Transformation" *Pua Plant Cell Reports* 1991, 10(6/7): 308-14.

Bates, *Molecular Biotechnol.*, 1994, 2(2):135-145.

Baulcombe, *Curr. Op. Plant Biol.*, 1999, 2:109-113.

Beachy et al., "A Genetic Map for the Cowpea Strain of TMV" *Virology* 1976, 73: 498-507.

Bedell et al., *J. Virol*, 1987, 61:3635-40.

Belanger et al., *Faseb J., 2000*, 14:2323-2328.

Bendahmane et al., *Proc, Natl. Acad. Sci.*, USA, 2002, 99:3645-3650.

Bhatnagar et al., "Anthrax Toxin" *Crit. Rev. Microbiol.*, 2001, 27(3): 167-200.
Boehm et al., *Ann, N.Y. Acad. Sci.*, 2007, 1102:121-134.
Bol et al., "A Functional Equivalence of Top Component A RNA and Coat Protein In The Initiation of Infection by Alfalfa Mosaic Villas" *Virology* 1971, 46: 73-85.
Bol et al., "Alfalfa Mosaic Virus and Ilarviruses: Involvement of Coat Protein in Multiple Steps of the Replication Cycle" *J. Gen. Viral.* 1999, 80: 1089-1102.
Brennan et al., *Microbiology*, 1999, 145:211-220.
Broothaerts et al., *Nature*, 2005, 433(7026):629-633.
Bruening et al., "*In Vitro* and *In Vivo* Translation of The Ribonucleic Acids of a Cowpea Strain of Tobacco Mosaic Virus" *Virology* 1976, 71: 498-517.
Buttery et al., *JR Coll. Physicians Land.*, 2000, 34:163.
Caddick et al., "An Ethanol Inducible Gene Switch for Plants Used to Manipulate Carbon Metabolism" *Nat. Biotechnol* 1998, 16: 177-180.
Calandrelli et al., *Res. Microbiol*, 2004, 155:283-9.
Callaway et al., *Ann. Rev. Phytopathol.*, 2001, 39:419-460.
Canizares et al., *Immunol. Cell Biol.*, 2005, 83:263-270.
Carrillo et al., *J. Viral.*, 1998, 72(2):1688-1690.
Chandler and Robertson, *Ann. Rev. Plant Physiol. Mol. Biol.*, 1994, 45:113-141.
Chen et al., *Current Microbiology*, 1992, 25:279-282.
Chen et al., *J. Bacteriology*, 1997, 179(19):6028-6034.
Chen et al., *Mol. Breed.*, 2003, 11, 287-293.
Chen et al., *Protein Expr. Purif.*, 2003, 32(2):239-45.
Chica et al., *Curr. Opin. Biotechnol.*, 2005, 16(4):378-84.
Chichester et al., *Vaccine*, 2007, 25:3111-3114.
Clemente et al., *Mol. Biotechnol.*, 2005, 30:41-50.
Conrad and Fiedler, *Plant Molecular Bio.*, 1998, 38:101-109.
Crameri et al., *Nature Biotechnol.*, 1996, 14(3):315-9.
Crossway, *Mol. Gen. Genet.*, 1986, 202:179-185.
Curtis and Nam, *Transgenic Research*, 2001, 10(4):363-371.
Dagan et al., *Mol. Biol. Evol.*, 2002, 19(7), 1022-1025.
Dalsgaard et al., *Nat. Biotechnol.*, 1997, 15:248-252.
Daniell et al..., *Trends Pl. Sci.*, 2001, 6:219-226.
Daniell, *Biotechnol. J.*, 2006, 1:1071-1079.
Dawson et al., *Proc. Natl Acad. Set., USA*, 1986, 83:1832.
Dawson et al., *Virology*, 1989, 172:285-92.
DeGraff, et al., "*In Vitro* Evidence That The Coat Protein of Alfalfa Mosaic Virus Plays A Direct Role in The Regulation of Plus and Minus RNA Synthesis Implications For The Life Cycle of Alfalfa Mosaic Virus" *Virology* 1995, 208: 583-589.
Dertzbaugh et al., *Infect. Immunol.*, 1993, 61:48.
Desfeux et al., *Plant Physiology*, 2000, 123(3):895-904.
Donson et al., *Proc. Natl. Acad. Sci.*, USA, 1991, 88:7204-7208.
Dreau et al., *Annals of Surgery*, 2000, 231:664-671.
Eckert et al., *PCR Methods and Applications*, 1991, 1:17.
English et al., *The Plant Cell* 1996, 8:179-188.
Filgueira etal., *Vaccine*, 2003, 21:42014209.
Fischer R. et al., Molecular farming of pharmaceutical proteins. *Transgenic Res.* 2000; 9(4-5):279-99.
Flick-Smith et al., *Infect. Imrnun.*, 2002, 70:1653-1656.
Flores et al., *Plant Physiol.*, 1993, 101:363-371.
Floss et al., *Transgenic Res.*, 2007, 16:315-322.
Fraley et al., "Liposome-Mediated Delivery of Tobacco Mosaic Virus RNA Into Tobacco Protoplasts: A Sensitive Assay For Monitoring Liposome-Protoplast Interactions" *Proc. Natl. Acad. Sci. USA* 1982, 79: 1859-1863.
Fraley et al., "Expression of Bacterial Genes in Plant Cells" *Proc. Natl. Acad. Sci. USA* 1983, 80: 4803-4807.
Franconi et al., *Cancer Res.*, 2002, 62:3654.
Franken etal., *Curr. Opin. Biotechnol.*, 1997, 8:411-416.
French et al., *Science*, 1986, 231:1294-97.
Fromm et al., "Expression of Genes Transferred Into Monocot and Dicot Plant Cells by Electroporation" *Proc. Natl. Acad. Sci. USA* 1985, 82: 5824, 1985.
Fujiyama et al. *J. Biosci. Bioeng.*, 2006, 101:398-402.
Gatz, et al., "Chemical Control of Gene Expression" *Ann. Rev. Plant. Physiol. Plant Mot Biol.* 1997, 48: 89-108, 1997.
Gelvin, Microbial. Mol Biol. Rev., 2003 67(1):16-37.
Gewolb, *Science*, 2002, 295:258-9.
Gigliotti et al., *J. Clin. Invest.*, 1982, 70:1306-9.
Gilleland et al, *FEMS Immunol. Med. Microbial.*, 2000, 27:291-297.
Gils et al., *Plant Biotechnol. J.*, 2005, 3:613-620.
Girl and Narasu, *Biotechnol, Adv.*, 2000, 18:1-22.
Gleba et al, *Current Opinion in Plant Biology*, 2004, 7:182-188.
Gleba et al, *Vaccine*, 2005, 23:2042-2048.
Gleba et al., *Curr. Opin. Biotechnol.*, 2007, 18:134-141.
Goldbach et al., *Meth. Plant Biochem.*, 1997, 10b:103-129.
Goldenkova et al., *Mol. Biol.*, 2002, 36:698-704.
Golovkin et al. *Proc. Natl. Acad. Sci. USA*, 2007, 104:6864-6869.
Gomord et al, *Plant J. Cell Mol Biol*, 1997, 11(2):313-325.
Grantham, *Science*, 1974, 185:862-864.
Grill et al., *Crit. Rev. Pl. Sci.*, 2005, 24:309-323.
Grimsley et al., *Proc. Natl. Acad. Sci., USA*, 1986, 83:3282-86.
Gu et al., *Vaccine*, 1999, 17:340.
Hahn et al., *Proc. Natl. Acad. Sci., USA*, 1994, 91(22):10417-10421.
Hamamoto et al., *Biotech.*, 1993, 11:930-932.
Hansen et al., *Biochim, Biophys. Acta.*, 1995, 1239(2):133-44.
Haq et al., *Science*, 1995, 268:714-716.
Haseloff et al., *Proc. Natl. Acad. Sci., USA*, 1997, 94(6):2122-2127.
Hatanaka et al., *Biochim. Biophys. Acta.*, 2004, 1696(1):75-82.
Hayes et al., *Nature*, 1988, 334:179.
Heffernan et al., *Am. J. Physiol. Endocrinal. Metab.*, 2000, 279:E501-E507.
Hellens et al., "pGreen: A Versatile and Flexible Binary Ti Vector for *Agrobacterium*-Mediated Plant Transformation" *Plant Molecular Biology* 2000, 42: 819-832.
Henne et al., *Nat. Biotechnol.*, 2004, 22(5:)547-53.
Hinchee et al., *Bio/Technol.*, 1988, 6:915-922.
Hobson et al., *J Hyg.*, 1972, 70:767.
Huang et al., *Vaccine*, 2005, 23:1851-1858.
Hull et al., *Vaccine*, 2005, 23:2082-2086.
Hunter et al., "Messenger RNA For The Coat Protein of Tobacco Mosaic Virus" *Nature* 1976, 260: 759-760.
Iqbal et al., *Biotechnol. Lett.*, 2003, 25 19 :1667-70.
Ishida et al., *FEBS Lett.*, 1999, 460(1):129-33.
Ishikawa et al., "In Vitro Mutagenesis of The Putative Replicase Genes of Tobacco Mosaic Virus" *Nucleic Acids Res.* 1986, 14: 8291-8308.
Jacobson et al., *Minerva Peditr.*, 2002, 54:295.
Jaspars et al., "Plant Viruses With a Multipartite Genome" *Adv. Virus Res.* 1974, 19; 37- 149.
Jefferson et al., *EMBO J.*, 1987, 6:3901-3907.
Johnson et al., *J. Virol.*, 2004, 78(10:6024-32.
Joshi, et al., "Context Sequences of Translation Initiation Codons in Plants" *Plant Molecular Biology* 1997, 35(6): 993-1001, 1997.
Kao et al., *Planta*, 1974,115:355.
Kapila et al., *Plant Sci.*, 1997, 122:101-108.
Kapusta et al., *FASEB J.*, 1999, 13:1796-1799.
Karlin and Altschul, *Proc. Natl, Acad, Sci., USA*, 1990, 87:2264-2268.
Karlin and Altschul, *Proc. Natl. Acad. Sci., USA*, 1993, 90:5873-5877.
Kelly et al., *Immunology*, 2000, 113:163.
Khandelwal et al., *Virology*, 2004, 323:284-291.
Kikkert et al., *In Vitro Cell, Dev. Bio. - Plant*, 1999. 35(1):43-50.
Kiyosue et al., *Plant J.*, 2000, 23:807-815.
Kjemtrup et al, *Plant J.*, 1998, 14(1):91 -100.
Klein et al., *Nature*, 327:70-73.
Klimpel, et al., "Anthrax Toxin Lethal Factor Contains A Zinc Metalloprotease Consensus Sequence Which Is Required for Lethal Toxin Activity" *Mol Microbiol* 1994, 13: 1093-1097.
Knapp et al., *J. Viral.*, 2001, 75:5518.
Knudsen and Muller, *Planta*, 1991, 185:330-336.
Koev and Miller, *J. Virology*, 2000, 74(13):5988-96.
Kohl et al., *Clin. Vaccine Immunol.*, 2006, 13:845-853.
Kohler and Milstein, *Nature*, 1975, 256:495.
Koo et al., *Proc. Natl. Acad. Sci., USA*, 1999, 96:7774-7779.
Koprowski and Yusibov, *Vaccine*, 2001, 19:2735-2741.
Koya et al., *Infect. Immun.*, 2005, 73:8266-8274.
Krens et al., *Nature*, 1982, 296:72-74.

Kumagai, et al., "Rapid, High-Level Expression of Glycosylated Rice α-Amylase In Transfected Plants by an RNA Viral Vector" *Gene* 2000, 245: 169-174.
Kumar et al. *Protein Expr Puril*, 2003, 32:10-17.
Lama et al., *Res. Microbiol.*, 2004, 155(4):283-9.
Lambkin et al., *Vaccine*, 2004, 22:4390.
Langeveld et al., *Vaccine*, 2001, 19:3661-3670.
Lawton et al., "Expression of a Soybean (3-Conelyeinin Gene Under The Control of The Cauliflower Mosaic Virus Virus 35S and 19S Promoters In Transformed Petunia Tissues" *Plant Mol. Biol* 1987, 9: 315-324.
Lee et al., *Appl. Environ. Microbiol.*, 2004, 70(3):1397-404.
Leslie et al., *Diabetologia*, 1999, 42:30-14.
Lewandowski and Dawson, *Virology*, 1998, 251:427-437.
Li et al., *Biotechnal. Lett.*, 2004, 26:953-7.
Liljeqvist et al., *J. Immunol. Methods*, 1997,210:125.
Lim et al., *Infection and Immunity*, 2005, 73:6547.
Little et al., *Infect. Immun.*, 1997, 65:5171-5175.
Loesch-Fries, et al., "Expression of Alfalfa Mosaic Virus RNA 4 cDNA Transcripts *In Vitro* and *In Vivo*" *Virology* 1985, 146: 177-187, 1985.
Lorenee and Verpoorte, *Methods Mol. Biol.*, 2004, 267:329-50.
Luo et al., *Plant J.*, 2000, 23:423-30.
Ma et al., "Transgenic Plants Expressing Autoantigens Fed to Mice to Induce Oral Immune Tolerance" *Nature Medicine* 1997, 3: 793-796.
Ma et al., *Eur. J. Immunol.*, 1994, 24:151-158.
Ma et al., *Science*, 1995, 268:716-719.
Maassab et al., *J. Infect. Dis.*, 1982, 146:780.
MacFarlane et al., *Virology*, 2000, 267:29-35.
Maliga et al., *Mol. Gen. Genet.*, 1976, 149, 267-271.
Mallory et al., *Nature Biotech.*, 2002, 20:622-625.
Marillionnet et al., *Proc. Natl. Acad. Sci., USA*, 2004, 101:6852-6857.
Marillionnet et al., *Nature Biotechnology*, 2005, 23:718-723.
Massa et al., *Vaccine*, 2007, 25:3018-3021.
Mathew, Plant Viruses Online (http://image.fs.uidaho.edu/vide/); downloaded Feb. 21, 2006.
Matsuhara et al., *The Plant Journal for Cell & Molecular Biology*, 2000, 22(1):79-86.
Mattila et al., *Nucleic Acids Res.*, 1991, 19:4967.
McCormick et al., "Rapid Production of Specific Vaccines for Lymphoma by Expression of the Tumor-Derived Single-Chain Fv Epitopes in Tobacco Plants" *Proc. Natl. Acad. Sci. USA* 1999, 96: 703-708.
McGarvey et al., *Biotech.*, 1995, 13:1484-1487.
Mellin et al., *International Journal of Cancer*, 2000, 89:300-304.
Menczel et al. *Theor. Appl. Genet.*, 1981, 59, 191-195.
Meshi et al., "Function of the 30 kd Protein of Tobacco Mosaic Virus: Involvement in Cell-To-Cell Movement and Dispensability for Replication" *EMBO J.* 1987, 6: 2557-63.
Mett et al., *Vaccine*, 2007, 25(16):3014-7.
Microbiology & Immunology: BS335: Plant Viruses, http://www-micro.msb.le.ac.uk/335/Plant.html; downloaded May 18, 2002.
Moayeri et al., *Curr. Opin. Microbiol.*, 2004, 7(1):19-24.
Modelska et al., *Proc. Nati. Acad. Sci., USA*, 1998, 95:2481-2485.
Moffat, *Science*, 1995, 268:658-660.
Molina et al., *Virology*, 2005, 342:266-275.
Moloney et al., *Plant Cell Rep.*, 1989, 8:238-242.
Moreira et al., *J. Basic Microbiology*, 2004, 44:29-35.
Mori et al., *Plant Journal*, 2001, 27(1):79-86.
Musiychuk et al., *Biochemistry (Mose)*, 2000, 65(12):1397-402.
Musiyehuk et al., *Influenza and Other Respiratory Viruses*, 2007, 1:1.
Nashar et al., *Vaccine*, 1993, 11:235.
Nass, Infect. *Dis. Clin. North Am.*, 1999, 13,187-208.
Neeleman et al., "Role of Alfalfa Mosaic Virus Coat Protein Gene in Symptom Formation" *Virology* 1991,181: 687-693.
Neeleman et al., "Infection of Tobacco With Alfalfa Mosaic Virus cDNAs Sheds Light On the Early Function of the Coat Protein" *Virology* 1993, 196: 883-887.
Nemchinov et al., *Arch. Virol.*, 2000, 145:2557-2573.
Okada, *Phil, Trans. Soc. Lond, B*, 1999, 354:569-582.
Ow, *Plant Molecular Bio.*, 2002, 48:183-200.
Palmer et al., *Vaccine*, 2006, 24:5516-5525.
Park et al., *Cancer*, 1995, 76:1902-1913.
Park et al., *J. Ind. Microbiol. Biotechnol.*, 2004, 31(4):189-97.
Parmenter D.L., "Production of biologically active hirudin in plant seeds using oleosin partitioning", *Plant Mol Biol.* 1995 Dec., 29(6):1167-80.
Peres et al., 2001 , *Plant Cell, Tissue, and Organ Culture*, 2001, 65:37-44.
Petosa et al., *Nature*, 1997, 385:833-838.
Pew Initiative on Food and Biotechnology, (Feb. 28, 2003), "Biopharming Could Reap Benefits but Must be Tightly Regulated," www. pewagbiotech.org.
Pfitzner et al., *Nucleic Acids Res.*, 1987, 15:4449.
Pilon-Smits et al., "Overexpression of ATP Sulfurylase In Indian Mustard Leads to Increased Selenate Uptake, Reduction, and Tolerance" *Plant Physiol.* 1999, 119(1): 123-132.
Piruzian et al., *Mol. Gen. Genet.*, 1998, 257(5):561-7.
Piruzian et al., *Mol. Genet. Genomics*, 2002, 266(5):778-786.
Piruzian et al., *Molecular Biology*, 2003, 37(4):554.
Pitson et al., *Enzyme and Microbial Technol.*, 1993, 15(3):178-192.
Pogue ct al., *Annu. Rev. Phytopathol.*, 2002, 40:45-74.
Pogue et al., *Pl. Mol. Biol. Manual.* 1998, L4, 1-27.
Porta et al., "Use of viral replicons for the expression of genes in plants", *Mol Biotechnol*. Jun. 1996; 5(3):209-21.
Potrykus et al., *Mol. Gen. Genet.*, 1985, 199:169-177.
Potter et al., *Br. J. Exp. Pathol.*, 1972, 53:168.
Potter et al., *Arch. Gesamte Virusforsch.*, 1973, 42:285.
Potter et al., *J. Hyq. Lond.*, 1973, 71:97.
Qing et al., "Transformation of Pakchoi (*Brassica rapa* L. ssp. *chinensis*) by *Agrobacterium* Infiltration", *Molecular Breeding*, 2000, 1:67-72.
Rao and Grantham, *Virology*, 1996, 226:294-305.
Rao and Ravishankar, *Biotechnol. Adv.*, 2002, 20:101-153.
Rennermalm et al., *Vaccine*, 2001, 19:3376-3383.
Richter et al., *Nat Biotechnol*, 2000, 18:1167-1171.
Riggs and Bates, *Proc. Natl. Acad. Sci.*, USA, 1986, 82:5602-5606.
Riva et al.,*EJB Electronic J. Biotech.*, 1998, 1(3), 118-133.
Saejung et al., *Vaccine*, 2007, 25:6646-6654.
Saito, et al., "Long-Distance Movement and Viral Assembly of Tobacco Mosaic Virus Mutants" *Virology* 1990, 176: 329-336.
Sanchez-Navarro et al., *Arch. Virol.*, 2001, 146:923-939.
Sanford, *Trends in Biotech.*, 1988, 6:299-302.
Santi et al., *Proc. Natl. Acad. Sci., USA*, 2006, 103(4):861-866.
Schell et al., "Transgenic Plants As Tools To Study the Molecular Organization of Plant Genes." *Science* 1987, 237: 1176-1183.
Schillberg et al., *Vaccine*, 2005, 23:1764-1769.
Schimming et al., *Eur. J. Biochem.*, 1992, 204(1):13-9.
Schob et al., *Mol. Gen. Genet.*, 1997, 256:581-585.
Scholthof and Seholthof, *Ann. Rev. Phytopathol.*, 1996, 34:299-323.
Schwechheimer et al., *Plant Molecular Bio.*, 1998, 36:195-204.
Seedorf et al., *Virology*, 1985, 145:181.
Shadwick and Doran, *Biotech. Bioen.*, 2006, 96:570 83.
Shadwick and Doran, *Journal of Biotechnology*, 2007, 131:318-329.
Shanks and Morgan, *Curr. Qp. in Biotech.*, 1999, 10:151-155.
Shima et al., *Biochem. Soc. Trans.*, 2004, 32:269-272.
Shivprasad et al., *Virology*, 1999, 255(2):312-23.
Singh et al., "The Chymotrypsin-Sensitive Site, FFD[315], In Anthrax Toxin Protective Antigen Is Required for Translocation of Lethal Factor" *J. Biol. Chem.* 1994, 269: 29039-29046.
Singh et al., *Infect. Immun.*,1998, 66, 3447-3448.
Sit et al., *Virology*, 2001, 75:9538-9542.
Smith et al., *Virology*, 2006, 348:475.
Soini et al., *Thorax*, 1996, 51:887-893.
Spitsin et al., *Proc. Natl. Acad. Sci., USA*, 1999, 96(5):2549-2553.
Srivastava, *Biotechnol. Adv.*, 1993, 11(3):441-65.
Staczek et al; *Vaccine*, 2000, 18:2266-2274.
Stahl et al., *Proc. Natl. Acad. Sci., USA*, 1989, 86:6283.
Sweet et al., *Microbial. Rev.*, 1980, 44:303.
Tacket et al., *J. Infect. Dis.*, 2000, 182:302-305.
Takamatsu et al., *FEBS Lett.*, 1990, 269:73-76.
Takamatsu et al., *EMBO J.*, 1987, 6:307-311.
Tanzer et al., *The Plant Cell*, 1997, 9:1411-1423.
Taschner et al., *Virology*, 1991, 181:445-450.
Thanavala et al., *Proc. Natl. Acad. Sci., USA*, 2005, 102:3378-3382.

Thomas et al., *Oncogene*, 1995, 10:261-8.
Thomas et al., *Plant J.*, 2001, 25:417-425.
Thomma et al., *Planta*, 2002, 216(2):193-202.
Timmermans et al., *Ann. Rev. Plant Physial. Plant Mal. Biol.*, 1994, 45:79-112.
Tobamoviruses, http://opbs.okstate.edu/virevol/tobamo.html; downloaded May 18, 2002.
Tomme et al., *J Bacterial.*, 1995, 177:4356-4363.
Torehilin et al., *Biochim Biophys Acta*, 2001, 1511(2):397-411.
Tregoning et al., *Phytochemistry*, 2004, 65:989-994.
Tsai et al., *J. Mol Biol.*, 2003, 330(3):607-20.
Tuboly etal., (2000), *Vaccine* 2000, 18:2023-2028.
Turpen et al., *J. Virol, Methods*, 1993, 42:227.
Turpen etal., *Biotechnology*, 1995, 13:53.
Turpen, *Phil. Trans. R. Soc. Lond. B.*, 1999, 354:665-73.
Ulrich et al., *Adv. Virus Res.*, 1998, 50:141.
Usha et al. "Expression of an animal virus antigenic site on the surface of a plant virus particle", *Virology*, 1993, Nov.; 197(1):366-74.
Van Der Kuyl et al., *Virology*, 1991, 183:731-738.
Van Der Kuyl et al., *Virology*, 1991, 185:496-499.
Van Der Vossen, et al., "Early and Late Functions of Alfalfa Mosaic Virus Coat Protein Can Be Mutated Separately" *Virology* 1994, 202: 891-903.
Van Rossura et al., *J. Virology*, 1997, 71:3811-3816.
Verch et al., *J. Immunal. Methods*, 1998, 220, 69-75.
Volten-Doting, Plant Viruses Online (http://image.fs.uidaho.edu/vide/descr009.htm) (downloaded May 18, 2002).
Voss et al., *Molecular Breeding*, 1995, 1:39-50.
Wang et al., *J. Bacteriology*, 2003, 185(14):4248-55.
Ward and Moo-Young, *Biotechnol. Adv.*, 1988, 6(1):39-69.
Waterhouse et al., *Nature*, 2001, 411:834-842.
Wei et al., (2002), *Journal of Northeast Forestry University*, 30:56-59 (English translation of specific passage referred to by Examiner in First Office Action of Chinese Application No. 03822979.X (national phase of PCT/ US2003/023520).
Weismuller et al., *Biol. Chem.*, 2001, 382(4):571-9.
Wigdorovitz et al., *Virology*, 1999, 255:347-353.
Wilson et al., *Nature*, 1981, 289:366.
Wu et al., *Vaccine*, 2003, 21:4390-4398.
Yang et al., *BMC Biotechnol.*, 2007, 7:62-72.
Yana and Poulos, *Curr. Opin. Biotechnol.*, 2003, 14(4):360-5.
Yusibov et al., "Antigens Produced in Plants by Infection With Chimeric Plant Viruses Immunize Against Rabies Virus and HIV-1" *Proc. Natl. Acad. Sci. USA* 1997; 94: 5784-5788.
Yusibov et al., "N-Terminal Basic Amino Acids of Alfalfa Mosaic Virus Coat Protein Involved in the Initiation of Infection" *Virology* 1995, 208: 405-407.
Yusibov, et al., "Functional Significance of Three Basic N-Terminal Amino Acids of Alfalfa Mosaic Virus Coat Protein" *Virology* 1998, 242: 1-5.
Yusibov et al, Plant Biotechnology: New Products and Applications (Eds. J. Hammond, P. McGarvey, and V. Yusibov), pp. 81-94, Springer-Verlag (1999).
Yusibov et al. *Curr. Top. Microbiol. Immunol*, 1999, 240:81-94.
Yusibov et al. *Drugs R&D*, 2006, 7:203-217.
Yusibov et al., *J. Gen. Virol.*, 1996, 77:567-573.
Yusibov et al., *Vaccine*, 2002, 20:3155-3164.
Yusibov et at., *Vaccine*, 2005, 23:2261-2265.
Zaitlin, Plant Viruses Online (littp://image.fs.uidaho.edu/vide/descr803.htm); downloaded Jul. 16, 2009.
Zhang et al., *Proc. Natl. Acad. Sci., USA*, 1991, 88:10252-10256.
Zhang, *J. Mol. Evol.*, 2000, 50:56-68.
Zumbach et al., *International Journal of Cancer*, 2000, 85:815-818.
Zuo and Chua, *Curr. Op. Biotechnol.*, 2000, 11:146-51.
International Search Report dated Jul. 8, 2004 for Int'l. Appln. No. PCT/US03/23520.
International Search Report dated Oct. 29, 2004 for Int'l. Appln. No. PCT/US03/35869.
International Search Report dated Oct. 22, 2004 for Int'l. Appln. No. PCT/US03/36056.
International Search Report and Written Opinion dated Mar. 28, 2005 for Int'l. Appln. No. PCT/USO4/03169.
International Search Report and Written Opinion dated Dec. 23, 2005 for lnt'l. Appln. No. PCT/USO4/16452.
International Search Report and Written Opinion dated May 5, 2006 for Int'l. Appln. No. PCT/US05/05409.
International Search Report and Written Opinion dated Jul. 26, 2007 for Int'l. Appln. No. PCT/US07/03250.
International Search Report and Written Opinion dated Apr. 4, 2008 for Int'l. Appln. No. PCT/US06/30545.
Office Action (Final) dated Jul. 28, 2008 for U.S. Appl. No. 10/294,314.
Office Action (Non-final) dated Jul. 27, 2007 for U.S. Appl. No. 10/294,314.
Office Action (Final) dated Jul. 20, 2006 for U.S. Appl. No. 10/294,314.
Office Action (Non-final) dated Oct. 14, 2005 for U.S. Appl. No. 10/294,314.
Office Action (Non-final) dated Sep. 11, 2006 for U.S. Appl. No. 10/770,600.
Supplementary Search Report dated Dec. 12, 2006 for European Appln. No. EP 04776107.7.
Supplementary Search Report dated Jul. 2, 2007 for European Appln. No. EP 04707807.6.
Supplementary Search Report dated Nov. 2, 2007 for European Appln. No. EP 03781904.2.
Supplementary Search Report dated Jul. 16, 2007 for European Appln. No. EP 03771957.2.
Supplementary Search Report dated Jul. 26, 2007 for European Appln. No. EP 03781869.7.

* cited by examiner

A1MV CP specific antibodies

GFP specific antibodies hGH specific antibodies

Modified B. Arthracis PA

```
tctagaaaacaATGGCTAAA..ATAGGATAAgagctc
       M  A  X   I  G  ^
```

FIG. 5

GUS staining after agro-infiltration of Mung bean sprout

GUS staining after agro-infiltration of Fenugreek sprouts

IA-2

FIGURE 9B Sprouts tested:
Brassicas

| | Latin Name | Variety | Common Name | Supplier |
|---|---|---|---|---|
| 1 | Brassica juncea | Tendergreen | Mustard Greens | Heirloom Seeds |
| 2 | Brassica juncea | Green Wave | Mustard Greens | Heirloom Seeds |
| 3 | Brassica juncea | Florida Broad Leaf | Mustard Greens | Heirloom Seeds |
| 4 | Brassica juncea | Southern Giant Curled | Mustard Greens | Heirloom Seeds |
| 5 | Brassica juncea | from NuCycle | Mustard Greens | NuCycle |
| 6 | Brassica juncea | Tendergreen | Mustard Greens, India | Burpee |
| 7 | Brassica oleracea | Russian Red Kale | Kale | Heirloom Seeds |
| 8 | Brassica oleracea | Dwarf Blue Curled Kale | Kale | Heirloom Seeds |
| 9 | Brassica oleracea | Early Siberian Kale | Kale | Heirloom Seeds |
| 10 | Brassica oleracea | Winter Red Kale | Kale | Heirloom Seeds |
| 11 | Brassica oleracea | Vates Collards | Collard Greens | Heirloom Seeds |
| 12 | Brassica oleracea | Georgia Collards | Collard Greens | Heirloom Seeds |
| 13 | Brassica oleracea | Morris Heading Collards | Collard Greens | Heirloom Seeds |
| 14 | Brassica oleracea | Early White Vienna | Kohlrabi | Heirloom Seeds |
| 15 | Brassica oleracea | Early Purple Vienna | Kohlrabi | Heirloom Seeds |
| 16 | Brassica | Seven Top | Turnip | Burpee |
| 17 | Brassica komatsuna | Tokyo | Japanese Spinach | Evergreen Y.H. Enterprises |
| 18 | Brassica botrytis | Snowball X | Cauliflower | American Seed |
| 19 | Brassica capitata | 'Early Golden Acre' | Cabbage | American Seed |
| 20 | Brassica rapa | Jade Pagoda | Chinese Cabbage | Agway |
| 21 | Paseolus angularis | | Adzuki beans | |
| 22 | Trifolium pratense | | Red clover | |
| 23 | Medicago sativa | | Alfalfa | |
| 24 | Phaseolus aureus | | Mung bean | |
| 25 | Trigonella foenum-graecum | | Fenugreek | |

PRODUCTION OF FOREIGN NUCLEIC ACIDS AND POLYPEPTIDES IN SPROUT SYSTEMS

RELATED APPLICATIONS

This application claims the benefit of U.S. Provisional Patent Application No. 60/652,186, filed Feb. 11, 2005. This application is a continuation in part application of U.S. patent application Ser. No. 10/294,314, filed Nov. 12, 2002. This application is a continuation in part application of U.S. patent application Ser. No. 10/770,600, filed Feb. 3, 2004 which claims the benefit of U.S. Provisional Application No. 60/444,615, filed Feb. 3, 2003. Each of the foregoing applications is hereby incorporated by reference in their entirety.

BACKGROUND OF THE INVENTION

The cost of pharmaceuticals is exorbitantly high and continues to rise. Some pharmaceuticals, in addition to their high cost, are also limited in supply, making it impossible for them to be available to every patient that needs them. This is particularly problematic in developing countries, where both cost and availability hinder the distribution of pharmaceuticals to needy populations.

Several factors contribute to the high costs of producing pharmaceuticals, and result in the high price of the pharmaceuticals for the consumer. A major contributing factor is the lack of economical means of producing the product. This is particularly true for protein and peptide-based medications. Another contributing factor for some medications is the inability to administer therapeutically effective amounts of the pharmaceutical agent orally. Many pharmaceuticals can only be administrated by injection into a particular site in the body. For example, many immunization medications for the treatment of allergies or infectious diseases require administration by injection. Protein and peptide pharmaceuticals, such as human growth hormone and insulin, can often only be administered by injection. Another factor that contributes to the cost of many pharmaceutical medications is their delivery to the hospital or distribution site. Particularly in hot climates, delivery and storage of pharmaceutical medications requires expensive refrigeration equipment. This is a major challenge in developing countries, where such equipment is often unavailable.

Pharmaceutical proteins and peptides have been produced in a wide variety of hosts. Many therapeutic proteins have been produced in heterologous expression systems including prokaryotes such as *Escherichia coli* and *Bacillus subtilis*, and eukaryotes such as yeast, fungi, insect cells, animal cells, and transgenic animals. Bacterial expression systems are relatively easy to manipulate and the yield of the product is high. However, mammalian proteins often require extensive posttranslational modification for functional activity, which can be a limiting factor in bacterial expression systems. Cell culture systems such as mammalian, human, and insect cell culture systems are more convenient for the production of complex proteins. However, long lead times, low recovery of the product, possible pathogen transfer, and high capital and production costs present serious concerns. Transgenic animals may provide an unlimited supply of complex proteins. Unfortunately, this system is limited by the long period of time it takes to generate new and improved products and the risk of pathogen transfer to human subjects.

The economic and biochemical limitations to producing pharmaceutical proteins and peptides in prokaryotic and eukaryotic cells, including high production costs, low yields, secretion problems, inappropriate modifications in protein processing, difficulties scaling up to larger volumes, and contamination have led researchers to examine plants as new hosts for the large-scale production of proteins and peptides with the expectation of reduced cost. Production of proteins in transgenic plants is described, for example, in U.S. Pat. Nos. 5,750,871; 5,565,347; 5,464,763; 5,750,871; and 5,565,347. Although plants are less expensive to grow and harvest in bulk than prokaryotic and eukaryotic cells, expression of the foreign gene in plant cells is typically low. In addition, harvesting the plant typically requires breaking the plants, for example, by removing the leaves, separating the stems from the roots, or removing the roots. Such breakage usually results, a process that initiates wilting of the plant part and apoptosis of the plant. A plant undergoing apoptosis generates proteases that contribute to the degradation of the transgenically expressed protein before purification of the protein is even begun. Even if the plant is to be directly consumed, the activity of the expressed pharmaceutical protein may be reduced by harvest-induced intercellular degradation machinery.

Another major concern associated with producing foreign proteins in transgenic plants that are grown in open fields is the possibility of cross-pollination with plants in the wild, making it possible for the foreign protein to enter the food chain. The complexity of governmental regulations surrounding agricultural practices for transgenic plants makes it difficult to get new transgenic plants approved for agricultural use. Furthermore, the outdoor environment is impossible to control, making proper growth, development, and regulation of foreign gene expression difficult to guarantee. For example, the induction of a heat inducible, light inducible, hormone inducible, or chemically inducible promoter would be practically impossible in an outdoor environment. Of course, the outdoor temperature and light levels cannot be controlled. Additionally, hormones or chemicals sprayed on a plant are likely to be dispersed not onto the plant, but into the environment by wind and rain. Spaying crop fields is also quite costly.

Rodriguez et al. (see U.S. Pat. Nos. 5,888,789; 5,889,189; and 5,994,628) disclose production of proteins, including pharmaceutical proteins, in grains such as barley or rice. Malting is a process by which grain is germinated under controlled conditions and in contained facilities to produce a product, e.g., a foreign protein product. The harvested product is the malted grain, which is typically kiln-dried at between 120° F. and 130° F. The developmentally regulated amylase promoter typically drives expression of foreign proteins in this system. Although the foreign proteins can be expressed in high quantities in this system, harvesting and administration of the protein usually requires processing of the malted grain, which can alter the quality of the expressed foreign protein.

There exists the need for a controlled regulatable system for producing pharmaceutical proteins in plants that decreases the amount of intercellular degradation of the expressed protein upon harvest.

SUMMARY OF THE INVENTION

The present invention provides methods for producing pharmaceutical proteins in sprouted seedlings, for example of the *Brassica* species, that can be consumed or harvested live. While the invention is described herein primarily in reference to its use for producing pharmaceutical proteins, the invention generally finds use for producing essentially any nucleic acid (DNA and/or RNA) and/or protein of interest, without limitation as to the particular use(s) of the nucleic acid or protein. For example, enzymes of use in any of a wide variety of industrial processes or bioremediation processes (e.g., enzymes that degrade pollutants) can be produced. Thus the description of the invention, and the claims, are to be considered as applying to any nucleic acid or protein of interest even if not explicitly indicated, including those with therapeutic applications and those without. In certain embodiments the protein is not a nutritionally important protein. Any particular protein may be excluded from the present invention without being named herein.

In certain preferred embodiments, the present invention involves growing a seed to an edible sprouted seedling in a contained, regulatable environment, e.g., indoors. The seed is preferably a genetically engineered seed that contains an expression cassette encoding a pharmaceutically active protein, or any protein or nucleic acid of interest, which expression is driven by an exogenously inducible promoter. According to the invention, a variety of exogenously inducible promoters can be used that are inducible, for example, by light, heat, phytohormones, nutrients, etc.

In related embodiments, the present invention provides methods of producing pharmaceutically active proteins in sprouted seedlings by first generating a seed stock for the sprouted seedling by transforming plants with an expression cassette that encodes pharmaceutically active protein using an *Agrobacterium* transformation system, wherein expression of the pharmaceutical protein is driven by a promoter, e.g., an inducible promoter. Transgenic seeds are obtained from the transformed plant, grown in a contained, regulatable environment, and the resulting sprouts express the pharmaceutical protein. If the promoter is inducible, expression begins following application of the appropriate inducer.

In other related embodiments methods are provided that involves infecting sprouted seedlings with a viral expression cassette encoding a pharmaceutically active protein whose expression is driven by a constitutive (or inducible) promoter. The sprouted seedlings are grown for two to fourteen days in a contained, regulatable environment or at least until sufficient levels of the pharmaceutical protein have been obtained for consumption or harvesting. The seedlings may or may not be transgenic seedlings. Thus in certain embodiments of the invention the genome of the seedlings comprises an expression cassette comprising a heterologous sequence that encodes a protein of interest or can be copied or transcribed to yield a nucleic acid of interest. The heterologous sequence may be operatively linked to expression signals (e.g., a promoter) sufficient to direct production of the protein or nucleic acid.

In certain embodiments of the invention in any of its aspects, trans-activation is used to induce or increase expression of a heterologous sequence. For example, the expression cassette can be an inactive expression cassette that comprises an inactive or silenced foreign nucleic acid sequence, which is capable of directing expression of a nucleic acid or polypeptide of interest upon its activation. In certain embodiments of the invention trans-activation is accomplished by infecting the sprouts with a recombinant plant viral vector (e.g., an RNA viral vector) that encodes a factor for activating or facilitating the expression of an inactive or silenced foreign nucleic acid sequence. See U.S. Ser. No. 10/832,603, entitled "Expression of Foreign Sequences in Plants Using Trans-Activation System", which is incorporated herein by reference, for further details of suitable methods. Such methods include techniques based on recombination (e.g., using a Lox/Cre or Flp/Frt recombinase system) and techniques based on proteins comprising a DNA binding domain such as GAL4 and a transcriptional activation domain such as VP16. It is noted that a variety of other methods may be used for achieving trans-activation. Thus using the trans-activation approach, expression is induced by an infection with an exogenously applied viral agent, but the inducer itself is produced within the host cell.

In certain embodiments of the invention in any of its aspects, the nucleic acid or protein of interest is post-transcriptionally and/or post-translationally processed in the cell in which it is expressed. In certain embodiments of the invention a protein of interest is secreted from the cell in which it is expressed. For example, the protein may naturally comprise a secretion signal sequence, or the coding region of a nucleic acid that encodes the protein may be modified to include a portion that encodes a secretion signal sequence. Secretion signal sequences are well known in the art.

In certain embodiments of the invention in any of its aspects a heterologous sequence that encodes a protein of interest may be altered to employ different codons from those present in the naturally occurring sequence, in order to improve expression in seedlings generally and/or in seedlings of a particular species. For example, the sequence may be codon optimized for expression in a particular species. Methods for performing codon optimization are known in the art.

The present invention further provides systems for producing pharmaceutically active proteins in sprouted seedlings that include a housing unit with climate control and a sprouted seedling containing an expression cassette that encodes a pharmaceutically active protein, wherein the pharmaceutically active protein is driven by a constitutive or inducible promoter. The inventive systems provide unique advantages over the outdoor environment or greenhouse, which cannot be controlled. This enables the grower to precisely time the induction of expression of the pharmaceutical protein. It also greatly reduces the cost of producing the pharmaceutical protein.

In a final embodiment, the present invention provides methods of treating a mammal with a pharmaceutically active protein expressed in sprouted seedlings by growing a seed to the sprouted seedling stage in a contained, regulatable environment, wherein the seed contains an expression cassette that includes an inducible promoter; inducing expression of the pharmaceutically active protein in the sprouted seedling; and administering the sprouted seedling expressing the pharmaceutically active protein to the mammal.

DEFINITIONS

"Administration" of a pharmaceutically active peptide or protein or a therapeutically active peptide or protein to a host in need thereof is intended as providing the pharmaceutically active protein to such host in a manner that retains the therapeutic effectiveness of such protein for a length of time sufficient to provide a desired beneficial effect to such host.

"Expression" refers to transcription and/or translation of an endogenous gene or a transgene in a plant, e.g., a sprout. The transgene may or may not be integrated into the genomic DNA of the plant. For example, "expression" refers to transcription and/or translation in a plant of a gene present in a bacterial, plasmid, or viral nucleic acid, regardless of whether the bacterial, plasmid, or viral nucleic acid is integrated into the genomic DNA of the plant. The gene may be a gene that is heterologous to the bacterium, plasmid, or virus.

"Expression cassette" or "expression vector" refers to a DNA sequence (or an RNA sequence in the case of RNA viruses or RNA plasmids), capable of directing expression of a particular nucleotide sequence in an appropriate host cell, including a promoter operably linked to the nucleotide sequence of interest, which is optionally operably linked to 3' sequences, such as 3' regulatory sequences or termination signals. It also typically includes sequences required for proper translation of the nucleotide sequence if any such sequences are needed. The coding region usually codes for a protein of interest but may also code for a functional RNA of interest, for example, an antisense RNA or a non-translated RNA that inhibits expression of a particular gene. The expression cassette including the nucleotide sequence of interest may be chimeric, meaning that the nucleotide sequence includes more than one DNA sequence of distinct origin that are fused together by recombinant DNA techniques, resulting in a nucleotide sequence that does not occur naturally and that particularly does not occur in the plant to be transformed. The expression cassette may also be one that is naturally occurring but has been obtained in a recombination form useful for heterologous expression. Typically, however, the expression cassette is heterologous with respect to the host, i.e., the particular DNA sequence of the expression cassette does not occur naturally in the host cell and must have been introduced into the host cell or an ancestor of the host cell by a transformation event. The expression of the nucleotide sequence in the expression cassette may be under the control of a constitutive promoter or of an inducible promoter that initiates transcription only when the host cell is exposed to some particular external stimulus. In the case of a multicellular organism, such as a sprouted seedling, the promoter can also be specific to a particular tissue, organ, or stage of development. A nuclear expression cassette is usually inserted into the nuclear genome of a plant and is capable of directing the expression of a particular nucleotide sequence from the nuclear genome of the plant. A plastid expression cassette is usually inserted into the plastid genome of a plant and is capable of directing the expression of a particularly nucleotide sequence from the plastid genome of the plant. In the case of a plastid expression cassette, for expression of nucleotide sequence from a plastid genome, additional elements, i.e., ribosome binding sites, or 3' stem-loop structures that impede plastid RNA polyadenylation and subsequent degradation may be required.

In certain embodiments of the invention the expression cassette comprises a promoter that is a minimal promoter such as a TATA element, and presence of a trans-activating factor may be necessary to direct expression of the nucleotide sequence, particularly to direct high level expression. For example, the expression cassette may comprise a DNA region for binding of a transcriptional activator. Such expression cassettes, and the promoters therein, are referred to as being "activatable".

A "gene" is a coding sequence and associated regulatory sequences, wherein the coding sequence is transcribed into RNA, such as mRNA, rRNA, tRNA, snRNA, sense RNA or antisense RNA. Examples of "regulatory sequences" are promoter sequences, 5' and 3' untranslated sequences, and termination sequences. In addition, introns and exons may also be included. In certain preferred embodiments, the gene is the coding sequence and the associated regulatory sequences are heterologous sequences.

A "food" or "food product" is a liquid or solid preparation of the sprouted seedlings of the invention that can be ingested by humans or other animals. Preferably, the terms include preparations of the raw or live sprouted seedlings and sprouted seedlings that may be fed live directly to humans and other animals. Materials obtained from a sprouted seedling are intended to include a whole edible sprouted seedling that can be ingested by a human or other animal. The term may also include any processed sprouted seedling together with a nutritional carrier that is fed to humans and other animals. Processing steps include steps commonly used in the food or feed industry. Such steps include, but are not limited to concentration or condensation of the solid matter of the sprouted seedling to form, for example, a pellet, production of a paste, drying, or lyophilization, or may be produced by cutting, mashing, or grinding of the plant to various extents, or by extraction of the liquid part of the plant to produce a soup, a syrup, or a juice. A processing step can also include cooking, e.g., steaming, the sprouted seedlings.

"Heterologous sequences," as used herein, means of different natural origin or of synthetic origin. For example, if a host cell is transformed with a nucleic acid sequence that does not occur in the untransformed host cell, that nucleic acid sequence is said to be heterologous with respect to the host cell. The transforming nucleic acid may include a heterologous promoter, heterologous coding sequence, or heterologous termination sequence. Alternatively, the transforming nucleic acid may be completely heterologous or may include any possible combination of heterologous and endogenous nucleic acid sequences. Similarly, heterologous refers to a nucleotide sequence derived from and inserted into the same natural, original cell type, but which is present in a non-natural state, e.g., a different copy number, or under the control of different regulatory elements. The term "heterologous" applies to cells, including plant and bacterial cells, and also to plasmids, plastids, and viruses.

A "host" is an animal to whom a pharmaceutically active protein of the present invention is administered. Such an animal is also referred to herein as a "subject". The term "animal" covers all vertebrates, life forms, humans, bovines, ovines, porcines, canines, felines, ferrets, rodents, primates, fish, birds, e.g., poultry and the like. Particularly preferred animals are mammals. The term "host" can also mean the cell (e.g., the plant cell) expressing the pharmaceutical protein.

An "inactive expression cassette" or "inactive expression vector" is a DNA or RNA sequence that comprises an inactive or silenced foreign nucleic acid sequence, which is capable of directing expression of a nucleic acid or polypeptide of interest upon its activation. Generally, an inactive expression cassette has the properties of an expression cassette as described above, except that the sequence that codes for a nucleic acid or polypeptide of interest may not be operatively linked to a promoter, e.g., it may be separated from the promoter (or from another regulatory element) by an intervening nucleic acid region. Operative linkage occurs following a recombination event, so that expression then occurs. Such as expression cassette is referred to as being "activatable".

The term "inducible promoter," means a promoter that is turned on by the presence or absence of a particular stimulus that increases promoter activity directly or indirectly. Some non-limiting examples of such stimuli include heat, light, developmental regulatory factors, wounding, hormones, and chemicals, e.g., small molecules. One example of a light-inducible promoter is the ribulose-5-phosphate carboxylase promoter. Chemically-inducible promoters also include receptor-mediated systems, e.g., those derived from other organisms, such as steroid-dependent gene expression, the Lac repressor system and the expression system utilizing the USP receptor from *Drosophila* mediated by juvenile growth hormone and its agonists, described in WO 97/13864, incorporated herein by reference, as well as systems utilizing combinations of receptors, e.g., as described in WO 96/27673, also incorporated herein by reference. Additional chemically inducible promoters include elicitor-induced promoters, safener-induced promoters as well as the alcA/alcR gene activation system that is inducible by certain alcohols and ketones (WO 93/21334; Caddick et al. (1998) *Nat. Biotechnol.* 16:177-180, the contents of which are incorporated herein by reference. Wond inducible promoters include promoters for proteinase inhibitors, e.g., proteinase inhibitor II promoter from potato, and other plant-derived promoters involved in the wound response pathway, such as promoters for polyphenyl oxidases, LAP, and TD. See, e.g., Gatz "Chemical Control of Gene Expression," *Ann. Rev. Plant Physiol. Plant Mol. Biol.* (1997) 48:89-108, incorporated herein by reference. Other inducible promoters include plant-derived promoters, such as the promoters in the systemic acquired resistance pathway, for example, PR promoters. It is noted that where inducible promoters are discussed herein, activatable promoters and expression cassettes can be used in a similar fashion in certain embodiments of the invention.

A "marker gene" is a gene encoding a selectable or screenable trait.

A "medical food" includes a composition that is eaten or drunk by a host and has a therapeutic effect on the host. A medical food includes, for example, a sprouted seedling of the present invention or plant matter derived thereof. A medical food may be ingested alone or may be administered in combination with a pharmaceutical composition well known in the medical arts. A medical food also includes the equivalent feedstuff for non-human animals.

"Operably linked" refers to components of a chimeric gene or an expression cassette that functions as a unit to express a heterologous protein. For example, a promoter operably linked to a heterologous DNA, which encodes a protein, promotes the production of functional mRNA corresponding to the heterologous DNA. A regulatory DNA sequence is said to be "operably linked to" or "associated with" a DNA sequence that codes for an RNA or a protein if the two sequences are situated such that the regulatory DNA sequence affects expression of the coding DNA sequence.

"Oral administration" of a pharmaceutically active peptide or protein means primarily administration by way of the mouth, preferably by eating, but also intends to include any administration that provides such peptides or proteins to the host's stomach or digestive track. In a preferred embodiment, oral administration results in contact of the pharmaceutically active protein with the gut mucosa.

A "pharmaceutically active protein" aids or contributes to the condition of a host in a positive manner when administered to the host in a therapeutically effective amount. A pharmaceutically active protein has healing curative or palliative properties against a disease and may be administered to ameliorate relieve, alleviate, reverse or lessen the severity of a disease. A pharmaceutically active protein also has prophylactic properties and is used to prevent the onset of a disease or to lessen the severity of such disease or pathological condition when it does emerge. Pharmaceutically active proteins include an entire protein or peptide or pharmaceutically active fragments thereof. It also includes pharmaceutically active analogs of the protein or peptide or analogs of fragments of the protein or peptide. The term pharmaceutically active protein also refers to a plurality of proteins or peptides that act cooperatively or synergistically to provide a therapeutic benefit. It is noted that the term "pharmaceutically active protein" includes proteins that comprise vaccine antigens, i.e., administration of the protein to a subject elicits a partially or fully protective immune response in the host. In certain embodiments of the invention the immune response protects the subject against an infectious agent, e.g., a virus, bacterial, fungal, or protozoal pathogen. Examples of vaccine antigens include hepatitis B surface antigen (HBsAg), *E. coli* heat-labile enterotoxin, rabies virus glycoprotein, and Norwalk virus capsid protein. In other embodiments of the invention the immune response protects the subject against a non-infectious condition or disease or lessens the severity of at least one sign or symptom of the condition or disease. Diseases of interest in this regard include, but are not limited to, cancer and auto-immune diseases. The term "pharmaceutically active protein" includes proteins that partially or fully tolerize a subject to exposure to an allergen that would otherwise elicit an allergic or anaphylactic response. A "pharmaceutically active nucleic acid" is a nucleic acid that encodes a pharmaceutically active protein or is pharmaceutically active in its own right, e.g., it has one or more pharmaceutical activities such as those described for pharmaceutically active proteins. For example, the nucleic acid may be one or more strands of an RNA interference (RNAi) agent. Such agents include short interfering RNAs (siRNAs), or short hairpin RNAs (shRNAs), or precursor of an siRNA or microRNA-like RNA, targeted to a target transcript, e.g., a transcript of an infectious agent or an endogenous disease-related transcript of a subject. An RNA interference A "promoter," as used herein, is a DNA sequence that initiates transcription of an associated DNA sequence. The promoter region may also include elements that act as regulators of gene expression such as activators, enhancers, and/or repressors.

"Regulatory elements" refer to sequences involved in conferring the expression of a nucleotide sequence. Regulatory elements include 5' regulatory sequences such as promoters that can be linked to the nucleotide sequence of interest, 3' sequences such as 3' regulatory sequences or termination signals. Regulatory elements also typically encompass sequences required for proper translation of the nucleotide sequence.

"Small molecules" are typically less than about one kilodalton and are biological, organic, or even inorganic compounds (e.g., cisplatin). Examples of such small molecules include nutrients such as sugars and sugar-derivatives (including phosphate derivatives), hormones (such as the phytohormones gibberellic or absisic acid), and synthetic small molecules.

"Specifically regulatable" refers to the ability of a small molecule to preferentially affect transcription from one promoter or group of promoters, as opposed to non-specific effects, such as enhancement or reduction of global transcription within a cell.

A "sprouted seedling" or "sprout" is a young shoot from a seed or a root, preferably a recently germinated seed. Preferably, the sprouted seedlings of the invention are edible sprouted seedlings or sprouts (e.g., alfalfa sprouts, mung bean sprouts, radish sprouts, wheat sprouts, mustard sprouts, spinach sprouts, carrot sprouts, beet sprouts, onion sprouts, garlic sprouts, celery sprouts, rhubarb sprouts, a leaf such as cabbage sprouts, or lettuce sprouts, watercress or cress sprouts, herb sprouts such as parsley or clover sprouts, cauliflower sprouts, broccoli sprouts, soybean sprouts, lentil sprouts, edible flower sprouts such as sunflower sprouts, etc.). According to the present invention, the sprouted seedling may have developed to the two-leaf stage. Generally, the sprouts of the invention are two to fourteen days old.

"Substantially isolated" is used in several contexts and typically refers to the at least partial purification of a protein or polypeptide away from unrelated or contaminating components (for example, plant structural and metabolic proteins). Methods for isolating and purifying proteins or polypeptides are well known in the art.

"Transformation" refers to introduction of a nucleic acid into a cell, particularly the stable integration of a DNA molecule into the genome of an organism of interest.

DESCRIPTION OF THE DRAWING

FIG. 5 is a schematic representation of transformation constructs for expression of recombinant proteins in *Brassica juncea*.

Figure depicts a schematic of a target gene engineered into agrobacterial expression system.

FIG. 8 demonstrates GUS staining after agro infiltration.

FIG. 9 demonstrates GUS staining after agro-infiltration of *Brassica* sprouts. FIG. 9B is a table of the sprouts tested in 9A.

DESCRIPTION OF CERTAIN PREFERRED EMBODIMENTS

Figure 1:
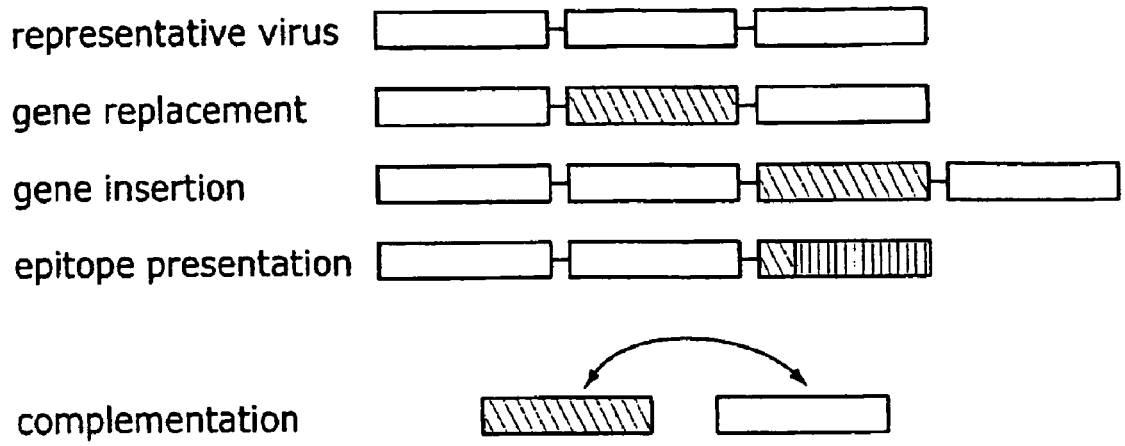
FIG. 1 is a schematic representation of different strategies for foreign gene expression using plant virus-based vectors.

The present invention provides systems and methods of producing pharmaceutical peptides and proteins in edible sprouted seedlings. The present invention further provides edible sprouted seedlings as a biomass containing a pharmaceutical peptide or protein. In certain preferred embodiments, the biomass is provided directly for consumption. In other preferred embodiments, the biomass is processed prior to consumption, for example, by homogenizing, crushing, drying, or extracting. In yet other preferred embodiments, the pharmaceutical protein is purified from the biomass and formulated into a pharmaceutical composition.

In certain preferred embodiments, genetically engineered seeds or embryos that contain a transgene encoding a pharmaceutical peptide or protein of interest are grown to the sprouted seedling stage in a contained, regulatable environment. In preferred embodiments, the contained, regulatable environment is a housing unit or room in which the seeds can be grown indoors. All environmental factors of the contained, regulatable environment may be controlled. Since sprouts do not require light to grow, and lighting can be expensive, in one particularly preferred embodiment, the genetically engineered seeds or embryos are grown to the sprouted seedling stage indoors in the absence of light.

Other environmental factors that can be regulated in the contained, regulatable environment of the present invention include temperature, humidity, water, nutrients, gas (e.g., $O_2$ or $CO_2$ content or air circulation), chemicals (small molecules such as sugars and sugar derivatives or hormones such as such as the phytohormones gibberellic or absisic acid, etc.) and the like.

According to the present invention, expression of the transgene encoding the pharmaceutical protein is preferably controlled by an exogenously inducible promoter. Exogenously inducible promoters are caused to increase or decrease expression of a transgene in response to an external, rather than an internal stimulus. A number of these environmental factors can act as inducers for expression of the transgenes carried by the expression cassettes of the genetically engineered sprouts. In certain preferred embodiments, the promoter is a heat-inducible promoter, such as a heat-shock promoter. For example, using as heat-shock promoter the temperature of the contained environment may simply be raised to induce expression of the transgene. Other promoters include light inducible promoters. Light-inducible promoters can be maintained as constitutive promoters if the light in the contained regulatable environment is always on. Alternatively, expression of the transgene can be turned on at a particular time during development by simply turning on the light. In yet other preferred embodiments, a chemically inducible promoter is used to induce expression of the transgene. According to these embodiments, the chemical could simply be misted or sprayed onto the seed, embryo, or seedling to induce expression of the transgene. Spraying and misting can be precisely controlled and directed onto the target seed, embryo, or seedling to which it is intended. The contained environment is devoid of wind or air currents, which could disperse the chemical away from the intended target, so that the chemical stays on the target for which it was intended.

According to the present invention, the time expression is induced is preferably selected to maximize expression of the pharmaceutical protein in the sprouted seedling by the time of harvest. Inducing expression in an embryo at a particular stage of growth, for example, inducing expression in an embryo at a particular number of days after germination, may result in maximum synthesis of the pharmaceutical protein at the time of harvest. For example, inducing expression from the promoter 4 days after germination may result in more protein synthesis than inducing expression from the promoter after 3 days or after 5 days. Those skilled in the art will appreciate that maximizing expression can be achieved by routine experimentation. In preferred embodiments, the sprouted seedlings are harvested at about 1, 2, 3, 4, 5, 6, 7, 8, 9, 10, 11, or 12 days after germination.

In cases where the expression vector has a constitutive promoter instead of an inducible promoter, the sprouted seedling may be harvested at a certain time after transformation of the sprouted seedling. For example, if a sprouted seedling were virally transformed at an early stage of development, for example, at the embryo stage, the sprouted seedlings may be harvested at a time when expression is at its maximum post-transformation, e.g., at about 1, 2, 3, 4, 5, 6, 7, 8, 9, 10, 11, 12, 13, or 14 days post-transformation. It could also be that sprouts develop one, two, three or more months post-transformation, depending on the germination of the seed.

Generally, once expression of the pharmaceutical protein begins, the seeds, embryos, or sprouted seedlings are allowed to grow until sufficient levels of the pharmaceutical protein are expressed. In certain preferred embodiments, sufficient levels are levels that would provide a therapeutic benefit to a patient if the harvested biomass were eaten raw. Alternatively, sufficient levels are levels from which the pharmaceutical protein can be concentrated or purified from the biomass and formulated into a pharmaceutical composition that provides a therapeutic benefit to a patient upon administration. Typically, the pharmaceutical protein is not a protein expressed in the sprouted seedling in nature. At any rate, the pharmaceutical protein is preferably expressed at concentrations above that which would be present in the sprouted seedling in nature.

In preferred embodiments, once expression of the pharmaceutical protein is induced, growth is allowed to continue until the sprouted seedling stage, at which time the sprouted seedlings are harvested. In a particularly preferred embodiment, the sprouted seedlings are harvested live. Harvesting live sprouted seedlings has several advantages including minimal effort and breakage. The spouted seedlings of the present invention are preferably grown hydroponically making harvesting a simple matter of lifting the sprouted seedling from its hydroponic solution. No soil is required for the growth of the sprouted seedlings of the invention, but may be provided if deemed necessary or desirable by the skilled artisan. Because sprouts can be grown without soil, no cleansing of sprouted seedling material is required at the time of harvest. Being able to harvest the sprouted seedling directly from its hydroponic environment without washing or scrubbing minimizes breakage of the harvested material. Breakage and wilting of plants induces apoptosis. During apoptosis, certain proteolytic enzymes become active, which can degrade the pharmaceutical protein expressed in the sprouted seedling, resulting in decreased therapeutic activity of the protein. Apoptosis-induced proteolysis significantly decreases the yield of protein from mature plants. Using the methods of the present invention, apoptosis is preferably (i.e., apoptosis is avoided) never induced because no harvesting takes place until the moment the proteins are extracted from the plant.

For example, live sprouts may be ground, crushed, or blended to produce a slurry of sprouted seedling biomass, in a buffer containing protease inhibitors. Preferably the buffer is at about 4° C. In other preferred embodiments, the sprouted seedling biomass is air-dried, spray dried, frozen, or freeze-dried. As in mature plants, some of these methods, such as air-drying, may result in a loss of activity of the pharmaceutical protein. However, because sprouted seedlings are very small and have a large surface area to volume ratio, this is much less likely to occur. Those skilled in the art will appreciate that many techniques for harvesting the biomass that minimize proteolysis of the pharmaceutical protein are available and could be applied to the present invention.

The sprouted seedlings are preferably edible. In particularly preferred embodiments, sprouted seedlings expressing sufficient levels of pharmaceutical proteins are consumed live so that absolutely no harvesting occurs before the sprouted seedlings are consumed. In this way, it is guaranteed that there is no harvest-induced proteolytic breakdown of the pharmaceutical protein before administration of the pharmaceutical protein to a patient in need of treatment. For example, sprouted seedlings that are ready to be consumed can be delivered directly to a patient. Alternatively, genetically engineered seeds or embryos are delivered to a patient in need of treatment and grown to the sprouted seedling stage by the patient. In one preferred embodiment, a supply of genetically engineered sprouted seedlings are provided to a patient, or to a doctor who will be treating patients, so that a continual stock of sprouted seedlings expressing certain desirable pharmaceutical proteins may be cultivated. This may be particularly valuable for populations in developing countries, where expensive pharmaceuticals are not affordable or deliverable. The ease with which the sprouted seedlings of the invention can be grown makes the sprouted seedlings of the present invention particularly desirable for such developing populations.

The regulatable nature of the contained environment imparts advantages to the present invention over growing plants in the outdoor environment. In general, growing genetically engineered sprouted seedlings that express pharmaceutical proteins in plants provides a pharmaceutical product faster (because the plants are harvested younger) and with less effort, risk, and regulatory considerations than growing genetically engineered plants. The contained, regulatable environment used in the present invention reduces or eliminates the risk of cross-pollinating plants in the nature.

For example, a heat inducible promoter could never be used in the outdoors because the outdoor temperature cannot be controlled. The promoter would be turned on any time the outdoor temperature rose above a certain level. Similarly, the promoter would be turned off every time the outdoor temperature dropped. Such temperature shifts could occur in a single day, for example, turning expression on in the daytime and off at night. A heat inducible promoter, such as those described herein, would not even be practical for use in a greenhouse, which is susceptible to climatic shifts to almost the same degree as the outdoors. Growth of genetically engineered plants in a greenhouse is quite costly. In contrast, in the present system, every variable can be controlled so that the maximum amount of expression can be achieved with every harvest.

In preferred embodiments, the sprouted seedlings of the present invention are grown in trays that can be watered, sprayed, or misted at any time during the development of the sprouted seedling. For example, the tray may be fitted with one or more watering, spraying, misting, and draining apparatus that can deliver and/or remove water, nutrients, chemicals etc. at specific time and at precise quantities during development of the sprouted seedling. For example, seeds require sufficient moisture to keep them damp. Excess moisture drains through holes in the trays into drains in the floor of the room. Preferably, drainage water is treated as appropriate for removal of harmful chemicals before discharge back into the environment.

Another advantage of the trays of the present system is that they can be contained within a very small space. Since no light is required for the sprouted seedlings to grow, the trays containing seeds, embryos, or sprouted seedlings may be tightly stacked vertically on top of one another, providing a large quantity of biomass per unit floor space in a housing facility constructed specifically for these purposes. In addition, the stacks of trays can be arranged in horizontal rows within the housing unit. Once the seedlings have grown to a stage appropriate for harvest (about two to fourteen days) the individual seedling trays are moved into a processing facility, either manually or by automatic means, such as a conveyor belt.

The system of the present invention is unique in that it provides a sprouted seedling biomass, which is a source of a pharmaceutically active protein. Whether consumed directly or processed into the form of a pharmaceutical composition, because the sprouted seedlings are grown in a contained, regulatable environment, the sprouted seedling biomass and/or pharmaceutical composition derived from the biomass can be provided to a consumer at low cost. In addition, the fact that the conditions for growth of the sprouted seedlings can be controlled makes the quality and purity of the product consistent. The contained, regulatable environment of the invention also obviates many safety regulations of the EPA that can prevent scientists from growing genetically engineered agricultural products out of doors.

Pharmaceuticals

The pharmaceutical proteins of the present invention, which are expressed in sprouted seedlings, include any pharmaceutical protein of interest, either prokaryotic or eukaryotic. Generally, the pharmaceutical proteins of interest include, but are not limited to, hormones (insulin, thyroid hormone, catecholamines, gonadotrophines, trophic hormones, prolactin, oxytocin, dopamine, bovine somatotropin, leptins and the like), growth hormones (e.g., human grown hormone), growth factors (e.g., epidermal growth factor, nerve growth factor, insulin-like growth factor and the like), growth factor receptors, cytokines and immune system proteins (e.g., interleukins, colony stimulating factor (CSF), granulocyte colony stimulating factor (G-CSF), granulocyte-macrophage colony stimulating factor (GM-CSF), erythropoietin, tumor necrosis factor (TNF), interfersons, integrins, addressins, seletins, homing receptors, T cell receptors, immunoglobulins, soluble major histocompatibility complex antigens, immunologically active antigens such as bacterial, parasitic, or viral antigens or allergens), autoantigens, antibodies), enzymes (tissue plasminogen activator, streptokinase, cholesterol biosynthetic or degradative, steriodogenic enzymes, kinases, phosphodiesterases, methylases, de-methylases, dehydrogenases, cellulases, proteases, lipases, phospholipases, aromatases, cytochromes, adenylate or guanylaste cyclases, neuramidases and the like), receptors (steroid hormone receptors, peptide receptors), binding proteins (sterpod binding proteins, growth hormone or growth factor binding proteins and the like), transcription and translation factors, oncoprotiens or proto-oncoprotiens (e.g., cell cycle proteins), muscle proteins (myosin or tropomyosin and the like), myeloproteins, neuroactive proteins, tumor growth suppressing proteins (angiostatin or endostatin, both which inhibit angiogenesis), anti-sepsis proteins (bectericidal permeability-increasing protein), structural proteins (such as collagen, fibroin, fibrinogen, elastin, tubulin, actin, and myosin), blood proteins (thrombin, serum albumin, Factor VII, Factor VIII, insulin, Factor IX, Factor X, tissue plasminogen activator, Protein C, von Wilebrand factor, antithrombin III, glucocerebrosidase, erythropoietin granulocyte colony stimulating factor (GCSF) or modified Factor VIII, anticoagulants such as huridin) and the like.

The present invention also provides pharmaceutical proteins for veterinary use, such as vaccines and growth hormones, which may be produced by the sprouted seedlings of the invention.

Suitable Plants

Those skilled in the art will appreciate that the plants that may be transformed in the present invention include any transformable plant of any stage of development (e.g., adult plants, seeds, seedlings etc.) that is edible as a seedling. In certain preferred embodiments, the plants of the invention may be plants of the *Brassica* or *Arabidopsis* species. Some suitable plants that are amendable to transformation and are edible as sprouted seedlings include alfalfa, mung bean, radish, wheat, mustard, spinach, carrot, beet, onion, garlic, celery, rhubarb, a leafy plant such as cabbage or lettuce, watercress or cress, herbs such as parsley, mint, or clovers, cauliflower, broccoli, soybean, lentils, edible flowers such as the sunflower etc.

Generating Transformed Sprouts

A variety of methods can be used to transform plant cells and produce genetically engineered sprouted seedlings. Two available methods for the transformation of plants that require that transgenic plant cell lines be generated in vitro, followed by regeneration of the cell lines into whole plants include *Agrobacterium tumefaciens* mediated gene transfer and microprojectile bombardment or electroporation. Viral transformation is a more rapid and less costly methods of transforming embryos and sprouted seedlings that can be harvested without an experimental or generational lag prior to obtaining the desired product. For any of these techniques, the skilled artisan would appreciate how to adjust and optimize transformation protocols that have traditionally been used for plants, seeds, embryos, or spouted seedlings.

*Agrobacterium* Transformation Expression Cassettes. *Agrobacterium* is a representative genus of the gram-negative family Rhizobiaceae. This species is responsible for plant tumors such as crown gall and hairy root disease. In dedifferentiated plant tissue, which is characteristic of tumors, amino acid derivatives known as opines are produced by the *Agrobacterium* and catabolized by the plant. The bacterial genes responsible for expression of opines are a convenient source of control elements for chimeric expression cassettes. According to the present invention, the *Agrobacterium* transformation system may be used to generate edible sprouted seedlings, which are merely harvested earlier than the mature plants. *Agrobacterium* transformation methods can easily be applied to regenerate sprouted seedlings expressing pharmaceutical proteins.

In general, transforming plants involves the transformation of plant cells grown in tissue culture by co-cultivation with an *Agrobacterium tumefaciens* carrying a plant/bacterial vector. The vector contains a gene encoding a pharmaceutical protein. The *Agrobacterium* transfers the vector to the plant host cell and is then eliminated using antibiotic treatment. Transformed plant cells expressing the pharmaceutical protein are selected, differentiated, and finally regenerated into complete plantlets (Hellens et al., *Plant Molecular Biology* (2000) 42(819-832); Pilon-Smits et al, *Plant Physiolog.* (January 1999) 119(1):123-132; Barfield and Pua *Plant Cell Reports* (1991)10(6/7):308-314); Riva et al., *Journal of Biotechnology* (Dec. 15, 1998) 1(3), each incorporated by reference herein.

Expression vectors for use in the present invention include a gene (or expression cassette) encoding a pharmaceutical protein designed for operation in plants, with companion sequences upstream and downstream of the expression cassette. The companion sequences are generally of plasmid or viral origin and provide necessary characteristics to the vector to transfer DNA from bacteria to the desired plant host.

The basic bacterial/plant vector construct preferably provides a broad host range prokaryote replication origin, a prokaryote selectable marker. Suitable prokaryotic selectable markers include resistance toward antibiotics such as ampicillin or tetracycline. Other DNA sequences encoding additional functions that are well known in the art may also be present in the vector.

Agrobacterium T-DNA sequences are required for Agrobacterium mediated transfer of DNA to the plant chromosome. The tumor-inducing genes of the T-DNA are typically removed and replaced with sequences encoding the pharmaceutical protein. The T-DNA border sequences are retained because they initiate integration of the T-DNA region into the plant genome. If expression of the pharmaceutical protein is not readily amenable to detection, the bacterial/plant vector construct will also include a selectable marker gene suitable for determining if a plant cell has been transformed, e.g., the nptII kanamycin resistance gene. On the same or different bacterial/plant vector (Ti plasmid) are Ti sequences. Ti sequences include the virulence genes, which encode a set of proteins responsible for the excision, transfer and integration of the T-DNA into the plant genome (Schell, *Science* (1987) 237:1176-1183). Other sequences suitable for permitting integration of the heterologous sequence into the plant genome may also include transposon sequences, and the like, for homologous recombination.

Certain constructs will include the expression cassette encoding the protein of interest. One, two, or more expression cassettes may be used in a given transformation. The recombinant expression cassette contains, in addition to the pharmaceutical protein encoding sequence, at least the following elements: a promoter region, plant 5' untranslated sequences, initiation codon (depending upon whether or not the expressed gene has its own), and transcription and translation termination sequences. In addition, transcription and translation terminators may be included in the expression cassettes or chimeric genes of the present invention. Signal secretion sequences that allow processing and translocation of the protein, as appropriate, may also be included in the expression cassette. A variety of promoters, signal sequences, and transcription and translation terminators are described, for example, in Lawton et al., *Plant Mol. Biol* (1987) 9:315-324 or U.S. Pat. No. 5,888,789, incorporated herein by reference. In addition, structural genes for antibiotic resistance are commonly utilized as a selection factor (Fraley et al. *Proc. Natl. Acad. Sci., USA* (1983) 80:4803-4807), incorporated herein by reference. Unique restriction enzyme sites at the 5' and 3' ends of the cassette allow for easy insertion into a pre-existing vector. Other binary vector systems for *Agrobacterium*-mediated transformation, carrying at least one T-DNA border sequence are described in PCT/EP99/07414, incorporated herein by reference. Further discussion of *Agrobacterium*-mediated transformation is found in Gelvin, S. B., "*Agrobacterium*-Mediated Plant Transformation: the Biology behind the "Gene-Jockeying" Tool", *Microbiology and Molecular Biology Reviews*, 67(1): 16-37 (2003), incorporated herein by reference, and references therein, all of which are incorporated herein by reference; Lorence A, Verpoorte R., Gene transfer and expression in plants. *Methods Mol Biol.* (2004) 267:329-50, incorporated herein by reference. In certain embodiments of the invention bacteria other than *Agrobacteria* are used to introduce a nucleic acid sequence into a plant. See, e.g., Broothaerts W, et al., Gene transfer to plants by diverse species of bacteria, *Nature* (2005), 433(7026):629-633, which is incorporated herein by reference.

Regeneration. Seeds of transformed plants are harvested, dried, cleaned, and tested for viability and for the presence and expression of a desired gene product. Once this has been determined, seed stock is stored under appropriate conditions of temperature, humidity, sanitation, and security to be used when necessary. Whole plants are then regenerated from cultured protoplasts, e.g., as described in Evans et al., *Handbook of Plant Cell Cultures*, Vol. 1:MacMillan Publishing Co. New York, 1983); and Vasil I. R. (ed.), *Cell Culture and Somatic Cell Genetics of Plants*, Acad. Press, Orlando, Vol. 1, 1984, and Vol. III, 1986, incorporated herein by reference. In preferred embodiments, the plants are regenerated only to the sprouted seedling stage. In other preferred embodiments, whole plants are regenerated to produce seed stocks and sprouted seedlings are generated from the seeds of the seed stock.

All plants from which protoplasts can be isolated and cultured to give whole, regenerated plants can be transformed by the present invention so that whole plants are recovered that contain the transferred gene. It is known that practically all plants can be regenerated from cultured cells or tissues, including, but not limited to, all major species of plants that produce edible sprouts. Some suitable plants include alfalfa, mung bean, radish, wheat, mustard, spinach, carrot, beet, onion, garlic, celery, rhubarb, a leafy plant such as cabbage or lettuce, watercress or cress, herbs such as parsley, mint, or clovers, cauliflower, broccoli, soybean, lentils, edible flowers such as the sunflower etc.

Means for regeneration vary from one species of plants to the next. However, those skilled in the art will appreciate that generally a suspension of transformed protoplants containing copies of the heterologous gene is first provided. Callus tissue is formed and shoots may be induced from callus and subsequently rooted. Alternatively, embryo formation can be induced from the protoplast suspension. These embryos germinate as natural embryos to form plants. Steeping the seed in water or spraying the seed with water to increase the moisture content of the seed to between 35-45% initiates germination. For germination to proceed, the seeds are typically maintained in air saturated with water under controlled temperature and airflow conditions. The culture media will generally contain various amino acids and hormones, such as auxin and cytokinins. It is also advantageous to add glutamic acid and proline to the medium, especially for such species as alfalfa. Shoots and roots normally develop simultaneously. Efficient regeneration will depend on the medium, the genotype, and the history of the culture. If these three variables are controlled, then regeneration is fully reproducible and repeatable.

The mature plants, grown from the transformed plant cells, are selfed and non-segregating, homozygous transgenic plants are identified. The inbred plant produces seeds containing the chimeric gene of the present invention. These seeds can be germinated and grown to the sprouted seedling stage to produce the pharmaceutical protein or polypeptide of interest.

In related embodiments, the seeds of the present invention are formed into seed products and sold with instructions on how to grow the seedlings to the appropriate sprouted seedling stage for administration or harvesting into a pharmaceutical composition. In other related embodiments, hybrids or novel varieties embodying the desired traits are developed from the inbred plants of the invention.

Direct Integration. Direct integration of DNA fragments into the genome of plant cells by microprojectile bombardment or electroporation may also be used in the present invention (see, e.g., Kikkert, J. R. Humiston et al., *In Vitro Cellular & Developmental Biology. Plant: Journal of the Tissue Culture Association*. (January/February 1999) 35 (1):43-50; Bates, G. W. Florida State University, Tallahassee, Fla. *Molecular Biotechnology* (October 1994) 2(2):135-145). More particularly, vectors containing a chimeric gene of the present invention can be introduced into plant cells by a variety of techniques. As described above, the vectors may include selectable markers for use in plant cells. The vectors may also include sequences that allow their selection and propagation in a secondary host, such as sequences containing an origin of replication and selectable marker. Typically, secondary hosts include bacteria and yeast. In one preferred embodiment, the secondary host is *Escherichia coli*, the origin of replication is a colE1-type origin of replication, and the selectable marker is a gene encoding ampicillin resistance. Such sequences are well known in the art and are commercially available (e.g., Clontech, Palo Alto, Calif. or Stratagene, La Jolla, Calif.).

The vectors of the present invention may also be modified to intermediate plant transformation plasmids that contain a region of homology to an *Agrobacterium tumefaciens* vector, a T-DNA border region from *Agrobacterium tumefaciens*, and chimeric genes or expression cassettes described above. Further vectors may include a disarmed plant tumor inducing plasmid of *Agrobacterium tumefaciens*.

According to the present embodiment, direct transformation of the vectors invention involves microinjecting the vectors directly into plant cells by the use of micropipettes to mechanically transfer the recombinant DNA (see, e.g., Crossway, *Mol. Gen. Genet.*, 202:179-185, 1985, incorporated herein by reference). The genetic material may also be transferred into the plant cell by using polyethylene glycols (see, e.g., Krens et al., *Nature* (1982) 296:72-74). Another method of introducing nucleic acid segments is high velocity ballistic penetration by small particles with the nucleic acid either within the matrix of small beads or particles, or on the surface (see, e.g., Klein et al., *Nature* (1987) 327:70-73; Knudsen and Muller *Planta* (1991) 185:330-336)). Yet another method of introduction is fusion of protoplasts with other entities, either minicells, cells, lysosomes, or other fusible lipid-surfaced bodies (see, e.g., Fraley et al., *Proc. Natl. Acad. Sci. USA* (1982) 79:1859-1863). Vectors of the invention may also be introduced into plant cells by electroporation (see, e.g., Fromm et al. *Proc. Natl. Acad. Sci. USA* (1985) 82:5824). According to this technique, plant protoplasts are electroporated in the presence of plasmids containing the gene construct. Electrical impulses of high field strength reversibly permeabilize biomembranes allowing the introduction of the pasmids. Electroporated plant protoplasts reform the cell wall divide and form plant callus, which can be regenerated to form the sprouted seedlings of the invention. Those skilled in the art would appreciate how to utilize these methods to transform plants cells that can be used to generate edible sprouted seedlings.

Viral Transformation. Expression and inexpensive recovery of peptides with adequate biological activity is important for different applications including development of subunit vaccines. Some applications, however, require full-length, biologically active proteins. Similarly to conventional expression systems, plant virus vectors can also be used to produce full-length proteins, including enzymes, blood component substitutes, and antibodies. According to the present invention, plant virus vectors are used to infect and produce foreign protein in seeds, embryos, sprouted seedlings. In this regard infection includes any method of introducing a viral genome, or portion thereof, into a cell, including, but not limited to, the natural infectious process of a virus, abrasion, inoculation, etc. The term includes introducing a genomic RNA transcript, or a cDNA copy thereof, into a cell. The viral genome need not be a complete genome but will typically contain sufficient sequences to allow replication. The genome may encode a viral replicase and may contain any cis-acting nucleic acid elements necessary for replication. Expression of high levels of foreign genes encoding short peptides as well as large complex proteins by tobamoviral vectors is described, for example, by McCormick et al. (*Proc. Natl. Acad. Sci. USA* (1999) 96:703-708; Kumagai et al. (*Gene* (2000) 245:169-174 and Verch et al. (*J. Immunol. Methods* (1998) 220, 69-75, each incorporated herein by reference). Thus, plant virus vectors have a demonstrated ability to express short peptides as well as large complex proteins.

In preferred embodiments, sprouts, which express pharmaceutical proteins such as insulin, GAD, and IA-2 associated with type 1 diabetes, are generated utilizing a host/virus system. Sprouts produced by viral infection provide a source of protein that has already been demonstrated to be safe. For example, sprouts are free of contamination with animal pathogens. Unlike, for example, tobacco, proteins from an edible sprout could at least in theory be used in oral applications without purification, thus significantly reducing costs. In addition, a virus/sprout system also offers a much simpler, less expensive route for scale-up and manufacturing, since the trangenes are introduced into the virus, which can be grown up to a commercial scale within a few days. In contrast, transgenic plants can require up to 5-7 years before sufficient seeds or plant material are available for large-scale trials or commercialization.

According to the present invention, plant RNA viruses have certain advantages, which make them attractive as vectors for foreign protein expression. The molecular biology and pathology of a number of plant RNA viruses are well characterized and there is considerable knowledge of virus biology, genetics, and regulatory sequences. Most plant RNA viruses have small genomes and infectious cDNA clones are available to facilitate genetic manipulation. Once the infectious virus material enters the susceptible host cell, it replicates to high levels and spreads rapidly throughout the entire sprouted seedling (one to ten days post inoculation). Virus particles are easily and economically recovered from infected sprouted seedling tissue. Viruses have a wide host range, enabling the use of a single construct for infection of several susceptible species. These characteristics are easily transferable to sprouts.

FIG. 1 illustrates several different strategies for expressing foreign genes using plant viruses. Foreign sequences can be expressed by replacing one of the viral genes with desired sequence, by inserting foreign sequences into the virus genome at an appropriate position, or by fusing foreign peptides to the structural proteins of a virus. Moreover, any of these approaches can be combined to express foreign sequences by trans-complementation of vital functions of a virus. A number of different strategies exist as tools to express foreign sequences in virus-infected plants using tobacco mosaic virus (TMV), alfalfa mosaic virus (AlMV), and chimeras thereof.

Figure 2:
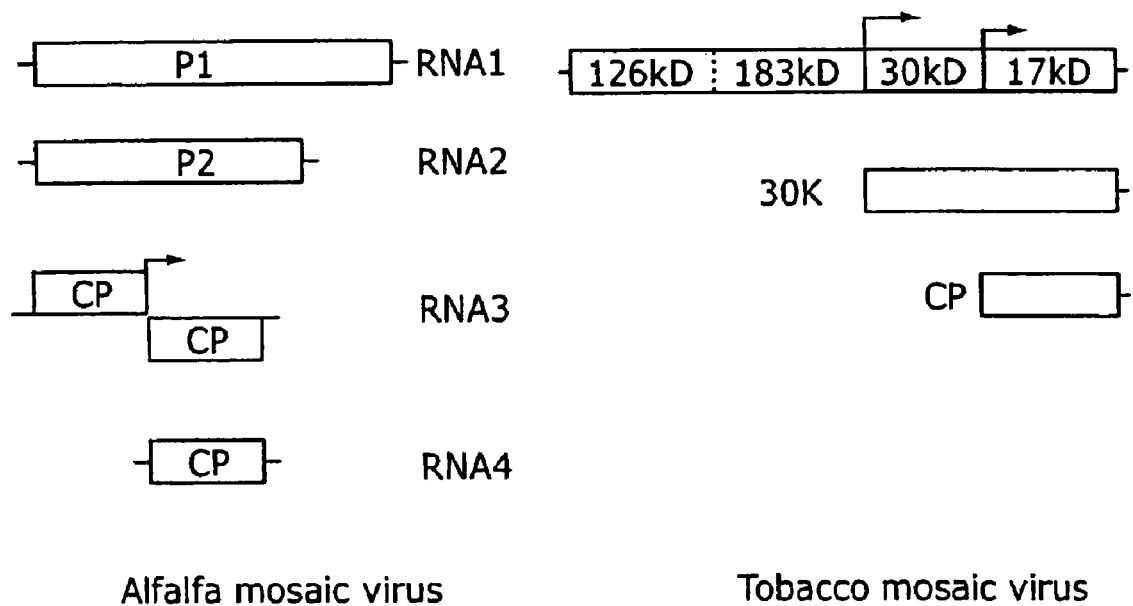
FIG. 2 is a schematic representation of AlMV and TMV genomes.

The genome of AIMV is a representative of the Bromoviridae family of viruses and consists of three genomic RNAs (RNAs1-3) and subgenomic RNA (RNA4) (FIG. 2). Genomic RNAs1 and 2 encode virus replicase proteins P1 and 2, respectively. Genomic RNA3 encodes the cell-to-cell movement protein P3 and the coat protein (CP). The CP is translated from subgenomic RNA4, which is synthesized from genomic RNA3, and is required to start the infection. Studies have demonstrated the involvement of the CP in multiple functions, including genome activation, replication, RNA stability, symptom formation, and RNA encapsidation (see e.g., Bol et al., *Virology* (1971) 46: 73-85; Van Der Vossen et al., *Virology* (1994) 202: 891-903; Yusibov et al., *Virology* 208: 405-407; Yusibov et al., *Virology* (1998) 242: 1-5; Bol et al., (Review, 100 refs.). *J. Gen. Virol.* (1999) 80: 1089-1102; De Graaff, *Virology* (1995) 208: 583-589; Jaspars et al., *Adv. Virus Res* (1974). 19, 37-149; Loesch-Fries, *Virology* (1985) 146: 177-187; Neeleman et al., *Virology* (1991) 181: 687-693; Neeleman et al., *Virology* (1993) 196: 883-887; Van Der Kuyl et al., *Virology* (1991) 183: 731-738; Van Der Kuyl et al., *Virology* (1991) 185: 496-499).

Encapsidation of viral particles is essential for long distance movement of virus from inoculated to un-inoculated parts of the seed, embryo, or sprouted seedling and for systemic infection. According to the present invention, inoculation can occur at any stage of plant development. In embryos and sprouts, spread of the inoculated virus should be very rapid. Virions of AIMV are encapsidated by a unique CP (24 kD), forming more than one type of particle. The size (30- to 60-nm in length and 18 nm in diameter) and shape (spherical, ellipsoidal, or bacilliform) of the particle depends on the size of the encapsidated RNA. Upon assembly, the N-terminus of the AIMV CP is thought to be located on the surface of the virus particles and does not appear to interfere with virus assembly (Bol et al., *Virology* (1971) 6: 73-85). Additionally, the AIMV CP with an additional 38-amino acid peptide at its N-terminus forms particles in vitro and retains biological activity (Yusibov et al., *J. Gen. Virol.* (1995) 77: 567-573).

AIMV has a wide host range, which includes a number of agriculturally valuable crop plants, including plant seeds, embryos, and sprouts. Together, these characteristics make the AIMV CP an excellent candidate as a carrier molecule and AIMV an attractive candidate vector for the expression of foreign sequences in the plant at the sprout stage of development. Moreover, upon expression from a heterologous vector such as TMV, the AIMV CP encapsidates TMV genome without interfering with virus infectivity (Yusibov et al., *Proc. Natl. Acad. Sci. USA* (1997) 94: 5784-5788, incorporated herein by reference). This allows the use of TMV as a carrier virus for AIMV CP fused to foreign sequences.

TMV, the prototype of the tobamoviruses, has a genome consisting of a single plus-sense RNA encapsidated with a 17.0 kD CP, which results in rod-shaped particles (300 nm in length) (FIG. 2). The CP is the only structural protein of TMV and is required for encapsidation and long distance movement of the virus in an infected host (Saito et al., *Virology* (1990) 176: 329-336). The 183 and 126 kD proteins are translated from genomic RNA and are required for virus replication (Ishikawa et al., *Nucleic Acids Res.* (1986) 14: 8291-8308). The 30 kD protein is the cell-to-cell movement protein of virus (Meshi et al., *EMBO J.* (1987) δ: 2557-2563). Movement and coat proteins are translated from subgenomic mRNAs (Hunter et al., *Nature* (1976) 260: 759-760; Bruening et al., *Virology* (1976) 71: 498-517; Beachy et al., *Virology* (1976) 73: 498-507, each incorporated herein by reference).

Schematic representation of AIMV and TMV genomes are shown in FIG. 2. RNAs1 and 2 of AIMV encode replicase proteins P1 and P2, respectively; genomic RNA3 encodes cell-to-cell movement protein P3 and the viral coat protein (CP). The CP is translated from subgenomic RNA4 synthesized from genomic RNA3. The 126 kD and 183 kD proteins of TMV are required for replication; the 30 kD protein is the viral cell-to-cell movement protein; and the 17 kD protein is the CP of virus. The CP and the 30 kD protein are translated from subgenomic RNAs. Arrows indicate position of subgenomic promoters.

Other methods of transforming plant tissues include transforming the flower of the plant. Transformation of *Arabidopsis thaliana* can be achieved by dipping the plant flowers into a solution of *Agrobacterium tumefaciens* (Curtis and Nam, *Transgenic Research* (August 2001) 10 4:363-371; Qing et al., *Molecular Breeding: New Strategies in Plant Improvement* (February 2000). (1):67-72). Transformed plants are formed in the population of seeds generated by the "dipped" plants. At a specific point during flower development, a pore exists in the ovary wall through which *Agrobacterium tumefaciens* gains access to the interior of the ovary. Once inside the ovary, the *Agrobacterium tumefaciens* proliferates and transforms individual ovules (Desfeux et al., *Plant Physiology* (July 2000) 123(3):895-904). The transformed ovules follow the typical pathway of seed formation within the ovary.

*Agrobacterium* Mediated Transient Expression

In additional aspects, the invention is directed to a combined approach of introducing viral expression vectors in sprouts via agroinfiltration to generate a transient expression system. *Agrobacterium* harboring an expression vector sequence encoding a target gene of interest. For transient transformation, non-integrated T-DNA copies remain transiently present in the nucleous and are transcribed leading to the expression of the carrying genes (Kapila et al., 1997). *Agrobacterium*-mediated transient expression, differently from viral vectors, cannot lead to the systemic spreading of the expression of the gene of interest. One advantage of this system is the possibility to clone genes larger than 2 kb to generate constructs that would be impossible to obtain with viral vectors (Voinnet et al., 2003). Furthermore, using such technique, it is possible to transform the plant with more than one transgene, such that multimeric proteins (e.g., antibodies subunits of complexed proteins) can be expressed and assembled. Furthermore, the possibility of co-expression of multiple transgenes by means of co-infiltration with different *Agrobacterium* can be taken advantage of, either by separate infiltration or using mixed cultures.

In preferred embodiments, an expression vector comprising viral genome sequence and further comprising sequence encoding a pharmaceutically active protein are introduced into *Agrobacterium*. Thus, binary vectors allow for selection in *Agrobacterium* as well as in cells which have been infiltrated with bacteria. Upon infiltration, viral DNA is transcribed to yield viral RNA production, followed by generation of viral proteins. Furthermore, production of viral proteins and viral RNA yields rapid production of multiple copies of RNA encoding the pharmaceutically active protein of interest. Such production results in rapid protein production of the target of interest in a relatively short period of time. Thus, a highly efficient system for protein production can be generated.

The agro-infiltration technique utilizing viral expression vectors can be used to produce limited quantity of protein of interest in order to verify the expression levels before deciding if it is worth generating transgenic plants. Alternatively, the agro-infiltration technique utilizing viral expression vectors is useful for rapid generation of plants capable of producing huge amounts of protein as a primary production platform. Thus, this transient expression system can be used on industrial scale.

Further provided are any of a variety of different Agrobacterial plasmids, binary plasmids, or derivatives thereof such as pBIV, pBI1221, pGreen, etc., which can be used in these and other aspects of the invention. Numerous suitable vectors are known in the art and can be directed and/or modified according to methods known in the art, or those described herein so as to utilize in the methods described provided herein.

Seeds

Still another aspect of the invention embodies seeds which can be generated and/or utilized for the methods described herein. Seeds transgenic for any gene of interest can be sprouted and chemically induced for production. A gene of interest is also referred to herein as a "target gene". Seeds capable of expressing any gene of interest can be sprouted and induced through: i) virus infection, ii) agroinfiltration, or iii) bacteria that contain virus genome. Seeds capable of expressing a transgene for heavy or light chain of any monoclonal antibody can be sprouted and induced for production of full-length molecule through: i) virus infection, ii) agroinfiltration, or iii) inoculation with bacteria that contain virus genome. Seeds capable of expressing a transgene for one or more components of a complex molecule comprising multiple components such as sIgA can be sprouted and used for producing a fully functional molecule through: i) virus infection, ii) agroinfiltration, or iii) inoculation with bacteria that contain virus genome. Seeds from healthy non-transgenic plants can be sprouted and used for producing target sequences through: i) virus infection, ii) agroinfiltration, or iii) inoculation with bacteria that contain a virus genome.

Administration and Pharmaceutical Compositions

The present invention provides a sprouted seedling expressing a pharmaceutically active protein that maintains its pharmaceutical activity when administered to a host in need thereof. Preferred hosts include vertebrates, preferably mammals, more preferably human. According to the present invention, the hosts include veterinary hosts such as bovines, ovines, canines, felines, etc. In preferred embodiments, the edible sprout is administered orally to a host in a therapeutically effective amount. In other preferred embodiments, the pharmaceutically active protein is provided in a pharmaceutical preparation, as described herein.

The pharmaceutical preparations of the present invention can be administered in a wide variety of ways to the host, such as, for example, orally enterally, nasally, parenterally, intramuscularly or intravenously, rectally, vaginally, topically, ocularly, pulmonarily, or by contact application. In a preferred embodiment, a pharmaceutical protein expressed in a sprout is administered to a host orally. In another preferred embodiment a pharmaceutically active protein expressed in a sprout is extracted and/or purified, and used for the preparation of a pharmaceutical composition. Proteins are isolated and purified in accordance with conventional conditions and techniques known in the art. These include methods such as extraction, precipitation, chromatography, affinity chromatography, electrophoresis, and the like.

The compositions of the present invention typically include an effective amount of a pharmaceutically active protein together with one or more organic or inorganic, liquid or solid, pharmaceutically suitable carrier materials. A pharmaceutically active protein produced according to the present invention is employed in dosage forms such as tablets, capsules, troches, dispersions, suspensions, solutions, capsules, creams, ointments, aerosols, powder packets, liquid solutions, solvents, diluents, surface active agents, isotonic agents, thickening or emulsifying agents, preservatives, solid bindings as long as the biological activity of the protein is not destroyed by such dosage form). Other examples of materials that can serve as pharmaceutically acceptable carriers include, but are not limited to sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening agents, flavoring agents, and perfuming agents, preservatives, and antioxidants can also be present in the composition, according to the judgment of the formulator (see also *Remington's Pharmaceutical Sciences*, Fifteenth Edition, E. W. martin (Mack Publishing Co., Easton Pa., 1975). For example, the protein may be provided as a pharmaceutical composition by means of conventional mixing granulating dragee-making, dissolving, lyophilizing, or similar processes.

In certain preferred embodiments it may be desirable to prolong the effect of a pharmaceutical preparation by slowing the absorption of the pharmaceutical protein that is subcutaneously or intramuscularly injected. This may be accomplished by the use of a liquid suspension of crystalline or amorphous material with poor water solubility. The rate of absorption of the protein then depends upon its rate of dissolution, which in turn, may depend upon size and form. Alternatively, delayed absorption of a parenterally administered protein is accomplished by dissolving or suspending the protein in an oil vehicle. Injectable depot forms are made by forming microencapsule matrices of the protein in biodegradable polymers such as polylactide-polyglycolide. Depending upon the ratio of protein to polymer and the nature of the particular polymer employed, the rate of release can be controlled. Examples of other biodegradable polymers include poly(orthoesters) and poly(anhydrides). Depot injectable formulations are also prepared by entrapping the protein in liposomes or microemulsions, which are compatible with body tissues.

Enterally administered protein preparations may be introduced in solid, semi-solid, suspension or emulsion form and may be compounded with any pharmaceutically acceptable carriers, such as water, suspending agents, and emulsifying agents. The proteins of the invention may also be administered by means of pumps or sustained-release forms, especially when administered as a preventive measure, so as to prevent the development of disease in a subject or to ameliorate or delay an already established disease.

The sprouted seedlings or pharmaceutically active proteins produced according to the present invention are particularly well suited for oral administration as pharmaceutical compositions. The harvested seedlings may be processed in a variety of ways, e.g., air drying, freeze drying, extraction etc., depending on the properties of the desired protein product and the desired form of the final product. In preferred embodiments, such compositions as described above are ingested orally alone or ingested together with food or feed or a beverage. Compositions for oral administration include sprouted seedlings; extractions of the sprouted seedlings, and proteins purified from sprouted seedlings provided as dry powders, foodstuffs, aqueous or non-aqueous solvents, suspensions, or emulsions. Examples of non-aqueous solvents are propylene glycol, polyethylene glycol, vegetable oil, fish oil, and injectable organic esters. Aqueous carriers include water, water-alcohol solutions, emulsions or suspensions, including saline and buffered medial parenteral vehicles including sodium chloride solution, Ringer's dextrose solution, dextrose plus sodium chloride solution, Ringer's solution containing lactose or fixed oils. Examples of dry powders include any sprouted seedling biomass that has been dried, for example, freeze dried, air dried, or spray dried. For example, the seedlings may be air dried by placing them in a commercial air dryer at about 120 degrees Fahrenheit until the biomass contains less than 5% moisture by weight. The dried seedlings are stored for further processing as bulk solids or further processed by grinding to a desired mesh sized powder. Alternatively, freeze-drying may be used for products that are sensitive to air-drying. Products may be freeze dried by placing them into a vacuum drier and dried frozen under a vacuum until the biomass contains less than about 5% moisture by weight. The dried material can be further processed as described herein.

Herbal preparations are well known in the art. Herbal preparations that may be used to administer the sprouts of the present invention include liquid and solid herbal preparations. Some examples of herbal preparations include tinctures, extracts (e.g., aqueous extracts, alcohol extracts), decoctions, dried preparations (e.g., air-dried, spray dried, frozen, or freeze-dried), powders (e.g., lyophilized powder), and liquid. Herbal preparations can be provided in any standard delivery vehicle, such as a capsule, tablet, suppository, liquid dosage, etc. Those skilled in the art will appreciate the various formulations and modalities of delivery of herbal preparations that may be applied to the present invention.

Those skilled in the art will appreciate that a particularly preferred method of obtaining the desired pharmaceutically active protein is by extraction. Fresh seedlings may be extracted to remove the desired protein products from the residual biomass, thereby increasing the concentration and purity of the product. Seedlings may also be extracted in a buffered solution. For example, the fresh harvested seedlings may be transferred into an amount of ice-cold water at a ratio of one to one by weight that has been buffered with, e.g., phosphate buffer. Protease inhibitors can also be added as required. The seedlings can be disrupted by vigorous blending or grinding while suspended in the buffer solution and the extracted biomass removed by filtration or centrifugation. The protein product carried in solution can be further purified by additional steps or converted to a dry powder by freeze-drying or precipitation. Extraction can also be carried out by pressing. Live seedlings can also be extracted by pressing in a press or by being crushed as they are passed through closely spaced rollers. The fluids expressed from the crushed plants are collected and processed according to methods well known in the art. Extraction by pressing allows the release of the products in a more concentrated form. However, the overall yield of the product may be lower than if the product were extracted in solution.

The sprouted seedlings, extractions, powders, dried preparations and purified protein products, etc., can also be in encapsulated form with or without one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active pharmaceutical protein may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

In other particularly preferred embodiments, a sprout expressing a pharmaceutically active protein of the present invention or biomass of sprouted seedlings is administered orally as medicinal food. Such edible compositions are consumed by eating raw, if in a solid form, or by drinking, if in liquid form. In a preferred embodiment, the plant material is directly ingested without a prior processing step or after minimal culinary preparation. For example, the pharmaceutically active protein is expressed in a sprout of which can be eaten directly. For example, the protein is expressed in an alfalfa sprout, mung bean sprout, or spinach or lettuce leaf sprout, etc. In an alternative embodiment, the sprouted seedling biomass is processed and the material recovered after the processing step is ingested.

Processing methods preferably used in the present invention are methods commonly used in the food or feed industry. The final products of such methods still include a substantial amount of the expressed pharmaceutically active protein and are preferably conveniently eaten or drunk. The final product may also be mixed with other food or feed forms, such as salts, carriers, favor enhancers, antibiotics, and the like, and consumed in solid, semi-solid, suspension, emulsion, or liquid form. In another preferred embodiment, such methods include a conservation step, such as, e.g., pasteurization, cooking, or addition of conservation and preservation agents. Any plant is used and processed in the present invention to produce edible or drinkable plant matter. The amount of pharmaceutically active protein in an edible or drinkable sprout preparation may be tested by methods standard in the art, e.g., gel electrophoresis, Elisa, or Western blot analysis, using an antibody specific for the protein. This determination is used to standardize the amount of protein ingested. For example, the amount of therapeutically active protein in a sprout juice determined and regulated, for example, by mixing batches of product having different levels of protein so that the quantity of juice to be drunk to ingest a single dose can be standardized. The contained, regulatable environment of the present invention, however, should minimize the need to carry out such standardization procedures.

A pharmaceutically active protein produced in a sprouted seedling and eaten by a host is absorbed by the digestive system. One advantage of the ingestion of a sprouted seedling or sprouted seedling preparation, particularly intact sprouts or sprout biomass that has been only minimally processed, is to provide encapsulation or sequestration of the protein in cells of the plant. Thus, the protein may receive at least some protection from digestion in the upper digestive tract before reaching the gut or intestine and a higher proportion of active would be available for uptake.

The pharmaceutical compositions of the present invention can be administered therapeutically or prophylactically. In certain preferred embodiments, the compositions may be used to treat or prevent a disease. For example, any individual who suffers from a disease or who is at risk of developing a disease may be treated. It will be appreciated that an individual can be considered at risk for developing a disease without having been diagnosed with any symptoms of the disease. For example, if the individual has a particular genetic marker identified as being associated with increased risk for developing a particular disease, that individual will be considered at risk for developing the disease. Similarly, if members of an individual's family have been diagnosed with a particular disease, e.g., cancer, the individual may be considered to be at risk for developing that disease.

Liquid dosage forms for oral administration include, but are not limited to, pharmaceutically acceptable emulsions, microemulsions, solutions, suspensions, syrups, and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Compositions for rectal or vaginal administration are preferably suppositories which can be prepared by mixing the compositions of this invention with suitable non-irritating excipients or carriers such as cocoa butter, polyethylene glycol or a suppository wax which are solid at ambient temperature but liquid at body temperature and therefore melt in the rectum or vaginal cavity and release the active protein.

Dosage forms for topical or transdermal administration of a pharmaceutical composition of this invention include ointments, pastes, creams, lotions, gels, powders, solutions, sprays, inhalants or patches. The active protein, or preparation thereof, is admixed under sterile conditions with a pharmaceutically acceptable carrier and any needed preservatives or buffers as may be required. Ophthalmic formulation, eardrops, and eye drops are also contemplated as being within the scope of this invention. Additionally, the present invention contemplates the use of transdermal patches, which have the added advantage of providing controlled delivery of a pharmaceutically active protein to the body. Such dosage forms can be made by suspending or dispensing the pharmaceutically active protein in the proper medium. Absorption enhancers can also be used to increase the flux of the pharmaceutically active protein across the skin. The rate can be controlled by either providing a rate controlling membrane or by dispersing the pharmaceutically active protein in a polymer matrix or gel.

The compositions are administered in such amounts and for such time as is necessary to achieve the desired result. As described above, in certain embodiments of the present invention a "therapeutically effective amount" of a pharmaceutical composition is that amount effective for treating, attenuating, or preventing a disease in a host. Thus, the "amount effective to treat, attenuate, or prevent disease", as used herein, refers to a nontoxic but sufficient amount of the pharmaceutical composition to treat, attenuate, or prevent disease in any host. As but one example, the "therapeutically effective amount" can be an amount to treat, attenuate, or prevent diabetes.

The exact amount required will vary from subject to subject, depending on the species, age, and general condition of the subject, the stage of the disease, the particular pharmaceutical mixture, its mode of administration, and the like. The sprouted seedlings of the invention and/or protein preparations thereof are preferably formulated in dosage unit form for ease of administration and uniformity of dosage. The expression "dosage unit form," as used herein, refers to a physically discrete unit of pharmaceutically active protein appropriate for the patient to be treated. It will be understood, however, that the total daily usage of the compositions of the present invention are preferably decided by an attending physician within the scope of sound medical judgment. The specific therapeutically effective dose level for any particular patient or organism will depend upon a variety of factors including the disorder being treated and the severity of the disorder; the activity of the specific compound employed; the specific composition employed; the age, body weight, general health, sex of the patient, diet of the patient, pharmacokinetical condition of the patient, the time of administration, route of administration, and rate of excretion of the specific compound employed; the duration of the treatment; drugs used in combination or coincidental with the specific compound employed; and like factors well known in the medical arts.

It will also be appreciated that the pharmaceutical compositions of the present invention can be employed in combination therapies, that is, the pharmaceutical compositions can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another anti-cancer agent), or they may achieve different effects.

Kits

In still another aspect, the present invention also provides a pharmaceutical pack or kit including the live sprouted seedlings of the present invention or preparations, extracts, or pharmaceutical compositions containing the pharmaceutically active protein expressed by the sprouted seedlings in one or more containers filled with one or more of the ingredients of the pharmaceutical compositions of the invention. In certain embodiments, the pharmaceutical pack or kit includes an additional approved therapeutic agent for use as a combination therapy. Optionally associated with such container(s) can be a notice in the form prescribed by a governmental agency regulating the manufacture, use or sale of pharmaceutical products, which notice reflects approval by the agency of manufacture, use, or sale for human administration.

The present invention involves the purification and affordable scaling up of the production of pharmaceutical proteins from sprouted seedlings using any of a variety of plant expression systems, most preferably viral plant expression systems. Kits are provided that include each protein in a diagnostic kit for genetic and immunologic diseases. In one preferred embodiment, the present invention provides kits having test samples of biological proteins and reagents for testing for the presence of antibodies in a patient's serum to those biological proteins. For example, the kit may provide IA-2 and GAD and reagents to test for the presence of excess amounts of antibodies to these proteins in a patient's serum, a clear indication of the presence or development of type 1 diabetes.

The present invention can be extended to provide diagnostic reagents in the form of a kit. As but one non-limiting example, the proteins insulin, GAD, and IA-2, associated with the autoimmune reaction in diabetes, can be provided as oral formulations and administered to induce oral tolerance to these proteins. Alternatively, one or more therapeutic protein can be provided in an injectable formulation or vaccine for administration. According to preferred embodiments, pharmaceutical doses or instructions therefor are provided in the kit for administration to an individual diagnosed with a disease, e.g., a diabetic individual, or an individual at risk for developing a disease, e.g., type 1 diabetes.

EQUIVALENTS

The representative examples that follow are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples which follow and the references to the scientific and patent literature cited herein. It should further be appreciated that the contents of those cited references are incorporated herein by reference to help illustrate the state of the art. The following examples contain important additional information, exemplification and guidance, which can be adapted to the practice of this invention in its various embodiments and the equivalents thereof.

EXAMPLES

Example 1

Production of Pharmaceuticals in Sprouts by *Agrobacterium* Transformation

Seeds of plants are transformed by *Agrobacterium* are harvested, dried, cleaned, and tested for viability and presence of desired genetic material. Seed stock is stored under appropriate conditions until use. At the time of use, appropriate amounts of seeds are soaked in water containing an amount of surface sterilizing agent (e.g., Clorox) for 20 minutes to 4 hours. Seeds are spread onto a flat of trays, which contain provisions for sustenance of growth and drainage of water. Trays containing the seeds are put on racks in the contained, regulatable environment under controlled temperature, lighting, access, air circulation, water supply, and drainage. Trays are misted with water from misters equipped with automatic timers for one to 30 minutes at intervals of 30 minutes to four hours, sufficient to keep seeds damp. Excess moisture drains through holes in the trays into drains in the floor of the room.

Seeds are allowed to germinate and develop under controlled conditions. Seeds are incubated for about two to fourteen days before harvest and processing. At some point during the incubation process, from four hours to seven days prior to harvest, seeds are exposed to environmental conditions that cause the induction of an introduced or indigenous DNA promoter sequence that causes an increase in the synthesis of one or more desired proteins in the tissues of the sprouting seedling. A transient increase in the incubation temperature from about 30° C. to about 37° C. to cause induction of a heat shock promoter.

After incubation of the seedlings for two to fourteen days, the seedlings are harvested by moving the individual trays into a processing facility on a conveyor belt. The harvested seedlings are processed by extraction in phosphate buffered solution containing protease inhibitors. The seedlings are disrupted by vigorous blending or grinding while suspended in the buffer solution and the extracted biomass removed by centrifugation.

Example 2

Sprouts of Seedlings Transiently Infected by a Plants Virus

Seeds of desired plants are obtained from a contract of commercial grower as wild-type seeds. The seed stock is stored under appropriate conditions of temperature, humidity, sanitation, and security until use. At the time of use, appropriate amounts of seeds are soaked in water and incubated on trays as described above under controlled conditions.

After incubation for two to fourteen days, the germinated seedlings are sprayed with a solution containing a virus harboring a transgene, and further or simultaneously treated with a material that causes mechanical abrasion of the plant leaf tissue. In this example, the leaves are abraded with a spray of air containing abrasive particles. The virus is allowed to systemically infect the plants for an appropriate period; from about one to about ten days and expression of the desired heterologous protein is monitored.

After infection of the seedlings for one to ten days, the seedlings are harvested as described in Example 1 above.

Example 3

Expression of Diabetes Associated Proteins and Human Growth Hormone in Plants

Early onset Type 1 or juvenile diabetes is a disease that affects children, adolescents, and young adults. Beta islet cells of the pancreatic endocrine system produce insulin in response to the metabolic signal of high blood glucose. The underlying etiology of the disease is the attack and destruction of the beta islet cells by the body's own immune system.

Individuals with type 1 diabetes produce antibodies against at least three proteins that are normally found in all individuals, i.e., insulin, glutamic acid decarboxylase (GAD), and the tyrosine-phosphatase-like protein IA-2 (Leslie et al., *Diabetologia* (1999) 42:30-14). Autoantibodies to the IA-2 and GAD proteins are found in 50 to 75% of type 1 diabetes patients prior to onset of the disease. In addition, the appearance of autoantibodies against these seemingly normal proteins occurs 7 to 8 years ahead of onset of the classical symptoms associated with type 1 diabetes.

Autoantigens such as insulin, GAD and IA-2 are useful in inducing at least a degree of oral tolerance to these proteins in susceptible individuals and prevent or reduce the damage to islet cells that results in the development of diabetes. Non-obese diabetic mice (NOD) spontaneously develop an autoimmune form of diabetes (Zahang, et al., *Proc. Natl. Acad. Sci. USA* (1991) 88:10252-10256). The gene encoding human insulin has been fused with the cholera toxin B subunit gene and the resulting construct expressed in transgenic potato plants. When these plants were fed to NOD mice, the animals showed a substantial reduction in pancreatic islet inflammation and a delay in the progression of diabetes (Arakawa et al., *Nat. Biotechnol.* (1998) 16:934-936). The GAD protein has also been expressed in potato plants. These transgenic potatoes, when fed to NOD mice, also either prevented or significantly delayed the onset of diabetes after 40 weeks (Ma et al., *Nature Medicine* (1997) 3:793-796).

In this example, certain non-limiting conditions for expression and recovery of GAD and IA-2 from plants are described. The GAD and IA-2 proteins are purified suing the His-tag method. Production of raw material and proteins takes place in two stages: 1) small scale (mg quantities) for preliminary studies in animals; and 2) medium scale (gram quantities for clinical trials.

Materials and Methods:

Testing the stability and movement. To conduct viral stability and movement tests, small quantities of each construct are synthesized. Each construct contains a T7 or SP6 RNA polymerase promoter fused to the exact 5' terminus of viral genomic RNA and a unique restriction site at the 3' end that is used to linearize the plasmid prior to in vitro transcription. The T7 or SP6 RNA polymerase then generates run-off transcripts, which are used to inoculate plants. Plants are inoculated mechanically at two-leaf stage, by gently rubbing the inoculum onto the leaf surface in the presence of an abrasive agent, such as carborundum powder (320-grit; Fisher, Pittsburgh, Pa.). Five to ten plants are inoculated per construct and 1-2 µg of each RNA transcript is used per inoculation. The plants are monitored for severity of symptoms, spread of virus throughout entire plant, and product recovery. At 10-15 days post infection (dpi) leaf samples from infected leaf samples are harvested to assess the presence of full-size recombinant IA-2 and GAD. A portion of the harvested material (10 leaves) is frozen in −80° C. and retained as a seed inoculum for the subsequent production scale-up of selected constructs. The rest of the tissue is processed immediately.

At 15-20 days post infection (dpi) recombinant IA-2 and GAD are recovered. The procedure is optimized to recover optimum quantities of high purity product (90-95% purity). Once products with the expected sizes are recovered and serological identity (recognized by specific antibodies using Western blot and ELISA) determined, the stability of the constructs is tested by three passages on healthy plants. Problems with assembly, recovery or stability of recombinant virus with proteins in the size range employed are manage at the level of nucleotide sequence or amino acid sequence by changing the conditions of infection or by using an alternative host plant.

Establishing seed-lot and procedures for medium scale production. When stage 1 is completed, a small quantity (100 ul) of in vitro synthesized transcripts of the recombinant constructs is prepared and used to inoculate 10 plants. Within 10-12 days after inoculation the leaves are harvested, tested for the presence of GAD or IA-2 by Western blot, and stored at −70° C. as seed material. A portion of this material (3-4) is used to inoculate 150-200 plants (1-2 kg of fresh tissue). Fifteen to twenty days after inoculation, recombinant protein is recovered and used for functional studies. An average of 60 mg of product per batch is expected.

Plant inoculation and product recovery. In vitro transcripts of recombinant virus containing GAD and IA-2 are synthesized using T7 RNA polymerase and purified plasmid DNA. Transcripts are capped using the RNA cap structure analog m7G(5)ppp(5)G. For inoculation, a mixture of in vitro transcription products is applied to the leaves of the target host plants after abrading the leaf surface with carborundum and gently rubbing on the leaf surface to spread the inoculum and further abrade the surface. The purity and activity of the plant produced IA-1 and GAD are tested. The antibody binding capacity of the plant-produced antigens is tested by ELISA during and after purification of the proteins.

Figure 4:
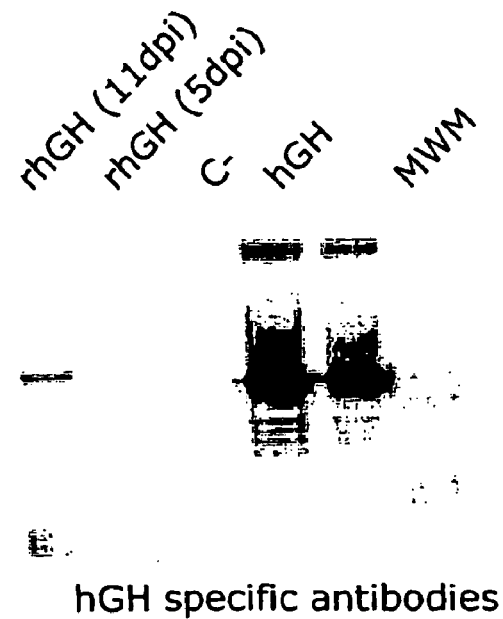
FIG. 4 is a picture of a Western blot of human growth hormone (hGH) production in *N. benthamiana* plants infected with in vitro transcripts of GH.
Figure 6:
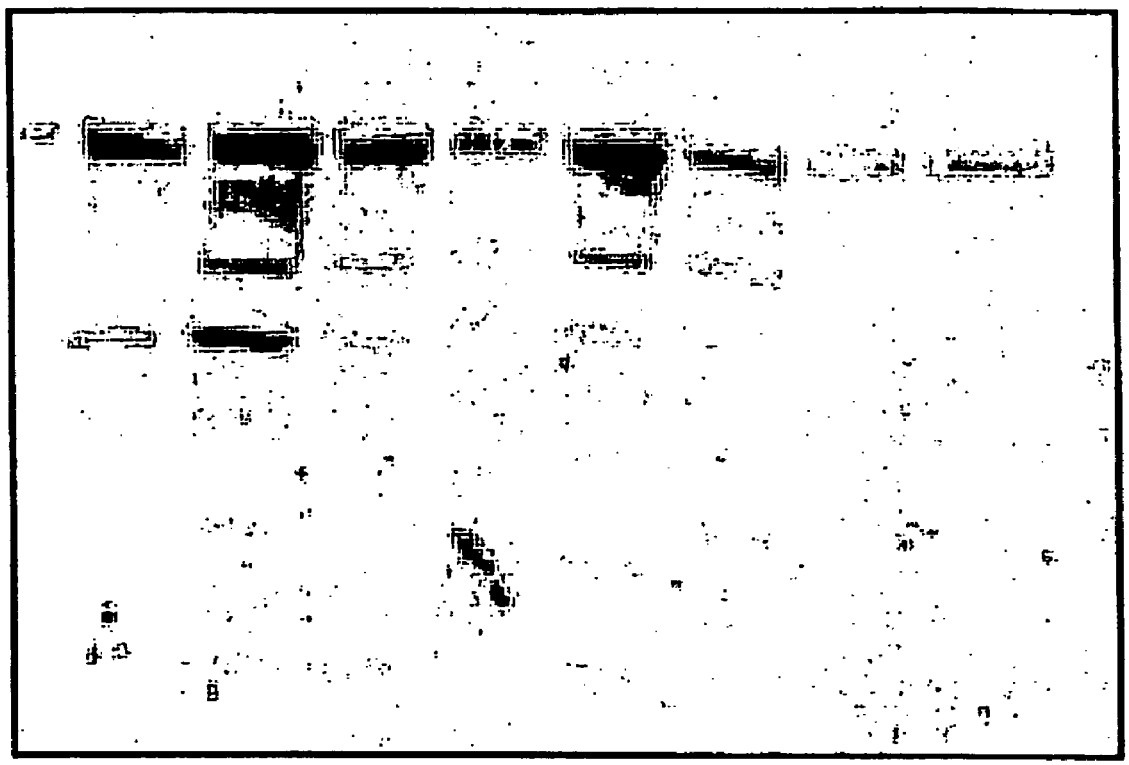
FIG. 6 is a picture of an immunoblot of transgenic *Brassica juncea* expressing human growth hormone under control of the HSP18.2 promoter.
Figure 7B:
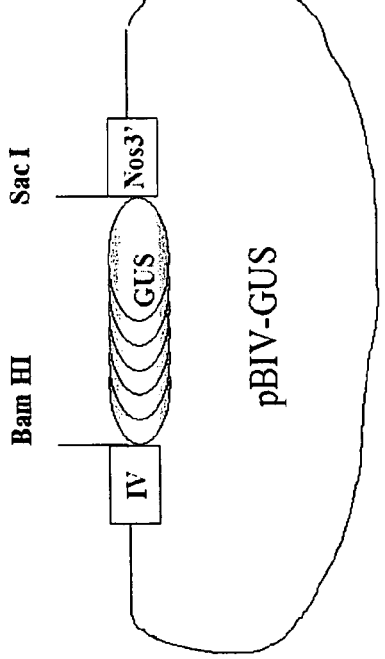
FIG. 7B depicts a schematic of a GUS gene.
Figure 7D:
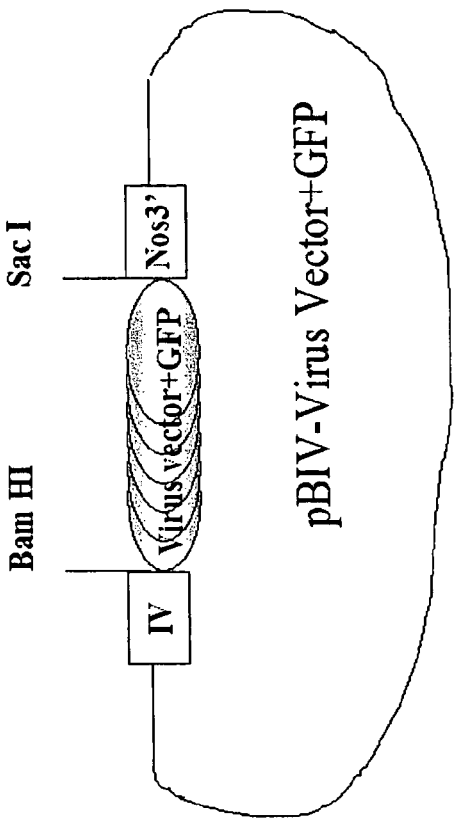
FIG. 7D depicts a plant virus or replicon containing GFP.
Figure 7A:
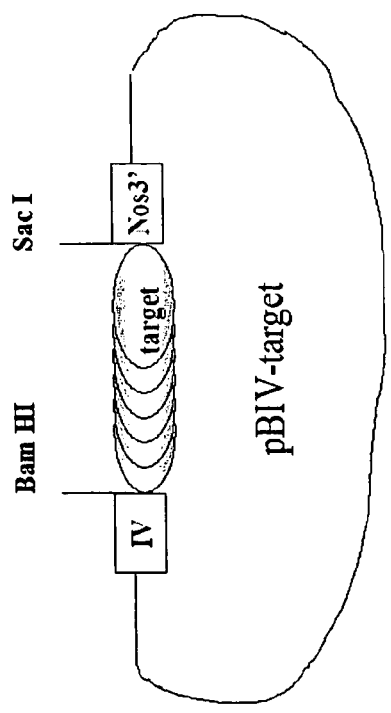
FIG. 7A: IV=any plant promoter, artificial promoter, or other promoter that functions in plant cells, e.g., a promoter of a plant virus such as cauliflower mosaic virus.
Figure 7C:
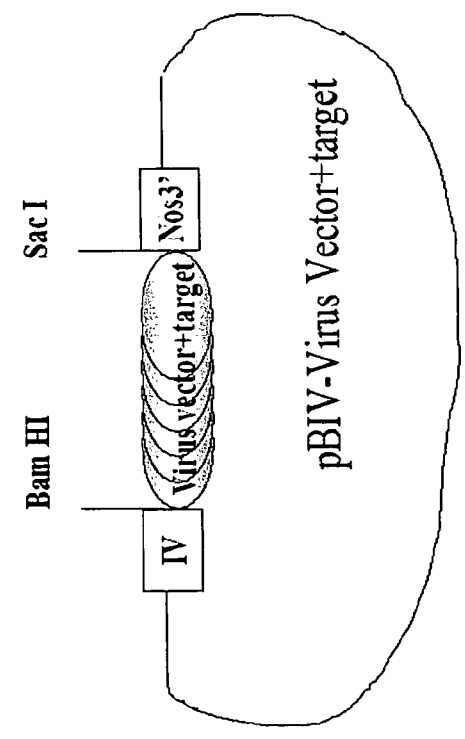
FIG. 7C depicts a plant virus vector or replicon containing target sequences engineered into the system.

Protein expression in *Nicotiana benthamiana*: To express full-length proteins in virus-infected plants, we used a functional complementation approach to express green fluorescent protein (GFP) from jellyfish in *N. benthamiana* plants (FIG. 4). During plant-to-plant passages, the amount of Alfalfa mosaic virus (Av)/GFP in the infected tissue gradually decreased and after the third transfer, only Av/A4 was detectable. (This is an advantage from an environmental safety point of view.) Using this approach, we could express an average of 100 µg of GFP per gram fresh tissue. An important component of this system, Alfalfa mosaic virus CP, is unique in its ability to encapsidate the genomic RNAs of unrelated viruses into infectious particles in the infected host. This unique ability of Alfalfa mosaic virus CP is exploited to engineer hybrid vectors that specifically target selected crop species.

Figure 3:
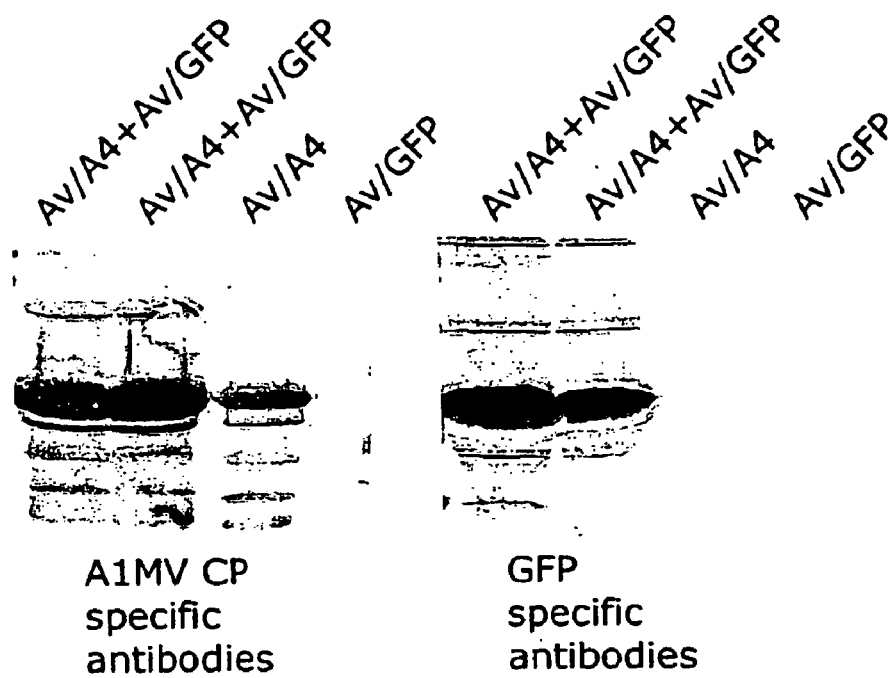
FIG. 3 is a picture of a Western blot of expression of recombinant GFP in *Necotiana benthamiana* plants inoculated with Av/A4 and Av A4GFP.

Expression of recombinant GFP in *Nicotiana benthamiana* plants inoculated with Av/A4 and Av/A4GFP was analyzed by Western Blot (see FIG. 3). Protein extracts from leaves infected systematically as described herein were separated by electrophoresis on a 12% SDS-polyacrylamide gel, transferred to a nitrocellulose membrane and reacted with protein-specific antibodies. Alfalfa mosaic virus CP-specific antibodies recognized the expected size protein (24.0 kD) in plants inoculated with Av/A4 or with the mixture of Av/A4 and Av/A4GFP. GFP-specific antibodies recognized protein only in extracts from plants inoculated with the mixture of Av/A4 and Av/A4GFP. GFP-specific antibodies did not react with any proteins in plants inoculated with only Av/A4. Neither Alfalfa mosaic virus CP- nor GFP-specific antibodies reacted with any protein in extracts from plants inoculated with Av/GFP only, suggesting the lack of systemic movement.

We have also engineered and expressed human growth hormone using this Av/A4 vector system. *Nicotiana benthamiana* plants were inoculated with in vitro transcripts and the plants monitored for production of hGH. No signal specific to the protein could be detected at 5 dpi (days post inoculation), although at 1 dpi we could detect a signal for hGH in the inoculated plants. FIG. 4 is a Western Blot of hGH produced in *N. benthamiana* plants infected with in vitro transcripts of 125C/hGH. Samples were analyzed 24 hours post inoculation. 1 µg of purified hGH was loaded as standard. MWM is molecular weight marker. The arrow in FIG. 4 points toward the hGH band on the blot detected by hGH-specific antibodies.

Example 4

Expression of Anthrax Associated Proteins and Human Growth Hormone in Plants

The virulence of anthrax is due to at least two major virulence factors. These factors are a polyglutamate capsule that helps protect the bacterium in the host and a three-part circulating toxin. Anthrax toxin is encoded by a 184 kb plasmid named pXO1 and consists of a receptor-binding protein named protective antigen (PA), and two enzymatically active proteins named edema factor and lethal factor (Bhatnagar and Batra. *Crit. Rev. Mirobiol*. (2001) 27(3):167-200).

In this example, two inactivated anthrax toxin components, protective antigen (PA) and lethal factor (LF) are produced in the leaves of *Brassica juncea* at concentration of at least 0.1 mg/gm dry weight. We have optimized the codon usage of these genes for plants and changed the amino acid sequences to minimize toxicity for both toxin molecules. We propose to insert the synthesized DNA into vectors capable of regulated gene expression in *Brassica juncea*. The PA gene was altered to delete phenylalanine residues at positions 314 and 315. The LF gene has an alanine substituted for a histidine at position 686 or position 690 (see, e.g., Singh et al., *J. Biol. Chem*. (1994) 269:29039-29046; Klimpel et al., *Mol. Microbiol*. (1994) 13: 1093-1097).

Transformation vector: The binary vector pGREENII 0229 (Hellens et al., *Plant Molecular Biology* (April 2000) 42(6): 819-832) is used for plant transformation (see FIG. 5). This plasmid includes the following components. 1) The pGREENII plasmid backbone includes sequences necessary for replication in *Escherichia coli* and *Agrobacterium tumefaciens*. 2) The *Agrobacterium tumefaciens* T-DNA left and right border (LB and RB) sequences are necessary for integration of all sequences between LB and RB into the plant genome. 3) The npt gene encoding kanamycin resistance for selection of *Escherichia coli* and *Agrobacterium* tumefacients tranformants. 4) The nos-bar gene, which encodes resistance to the herbicide Bialaphos (resistance to Bialophos is used to select transgenic plants. The nos-bar gene is transcribed from the Cauliflower mosaic virus (CAMV) 35S promoter with constitutive activity in plants, and transcription of the gene is terminated using the CaMV terminator. 5) Expression of vir genes PA and LF are driven either by the CAMV 35S promoter as shown in FIG. 5, or by the HSP18.2 promoter (GenBank accession # X17295, locus At5g59720) for the *Arabidopsis thaliana* low molecular weight heat shock protein (Matsuhara et al., *The Plant Journal: for Cell & Molecular Biolog* (April 2000) 22(1):79-86). Transcriptional termination is mediated by the terminator of the nopaline synthase gene (nos). The 35S and HSP18.2 promoters where chosen for their differing activities. The 35S promoter is constitutively active in most plant tissues. In many cases the 35S promoter drives high-level expression of the protein of interest. By contrast the HSP18.2 promoter is nearly inactive unless the plants are challenged by heat shock. High-level expression of some proteins can only be achieved using an inducible promoter system.

Vector construction and plant transformation. The vectors are constructed using DH5, a laboratory strain of *Escherichia coli*. The construction is analyzed by restriction endonuclease mapping and sequencing. After construction is confirmed the vector is used to transform *Agrobacterium tumefaciens* strain GV3101, lacking a native Ti plasmid and suitable for transfer of the TDNA of binary vectors into plants. *Brassica juncea* plants are transformed by introduction of GV3101 carrying the transformation vector into flowers by any available transformation method.

Modifications introduced into PA and LF genes. The nucleotide sequences of both PA and LF are modified for expression in plants. The coding sequence of native PA is 2295 bp and native LF is 2430 bp. These sequences are modified as follows: 1) Mutations are introduced that render PA and LF inactive as toxins. Phe314 and Phe315 are deleted from PA and His686 and His690 are mutated to Ala. 2) Codon usage is optimized for expression in *Brassica juncea*. Since the codon usage and GC/AT ratio of *Brassica juncea* is neutral the changes introduced into PA and LF are not extensive. Four codons are changed in PA and seven in LF. 3) Unique restriction sites are added to the 5' and 3' ends of the genes for cloning into the plant expression vector. [4] A consensus sequence for translation initiation will be added (Joshi et al., *Plant Molecular Biology*. (December 1997) 35(6):993-1001). The restriction sites and optimized translation initiation site are illustrated in FIG. 5. The 5' end shows the added XbaI restriction site and the consensus translation initiation site for plant genes, which includes the initiation codon followed by an Ala codon. The 3' end shows the added SacI restriction site. The modified PA and LF genes are chemically synthesized by Entelechon, Inc. (Regensburg, Germany).

A second construction is also produced for PA and LF. The intention of the second construct is to optimize the accumulation for PA and LF by targeting and retaining the proteins in the endoplasmic reticulum[40]. Targeting and retention in the ER has the potential to produce high-level accumulation of a recombinant protein (Haseloff, et al., *Proceedings of the National Academy of Sciences USA*. (Mar. 18, 1997) 94(6): 2122-2127). To achieve this, an amino-terminal signal sequence and a carboxyl terminal ER retention sequence is added. The signal sequence includes 22 codons derived from the *Arabidopsis thaliana* chitinase gene (Haseloff, et al., supra). The ER retention sequence is the tetrapeptide HisAspGluLeu (Gomord et al, *The Plant Journal: for Cell & Molecular Biology*. (February 1997) 11(2):313-325). The signal sequence is added by PCR stitching using the synthetic genes produced by Entelechon as templates (Tomme et al., *J. Bacteriol*. (1995) 177:4356-4363). The ER retention sequence is added by PCR amplification of the PA and LF genes using a 3' primer into which the HisAspGluLeu coding sequence has been incorporated. Modified PA and LF sequences are cloned into 35S and HSP18.2 expression vectors. Two modified version of each PA and LF (a total of 4) are cloned. In total, 8 different constructions are tested.

Selection and analysis of plants expressing transgenes. After transformation of *Brassica juncea* with *Agrobacterium tumefaciens* strain GV3101 carrying the transformation construct the plants are allowed to progress through their normal developmental program. Within 25 days, mature seeds are produced, dried, and harvested. The seeds are sown in potting soil and seedling plants are grown for 15 days. The leaves of each plant are then sprayed with a 0.0058% (w/v) solution of Bialophos (FINALE, Farnam, Inc., Phoenix, Ariz.). Sensitive, non-transgenic plants are typically killed within 5 to 7 days. Bialophos-resistant plants are evident by their green and healthy appearance. The putative transgenic plants are confirmed and analyzed using a series of protocols. Polymerase chain reaction using oligonucleotide primers specific for the construct are used to confirm the presence of the TDNA in putative transgenic plants. The presence of the TDNA is then be examined by blotting of genomic DNA using a specific DNA probe, the modified PA or LF genes. Finally, expression of the protein of interest is examined by SDS-PAGE followed by staining with Coomassie Blue or immunoblotting. The protocol for analysis of protein expression differs depending upon the construct used to produce the transgenic plant. Plants carrying 35S promoter constructions are analyzed directly since expression from this promoter is constitutive. Plants carrying the HSP18.2 promoter are heat shocked before analysis. The kinetics of recombinant protein expression might differ in different transgenic plants. Ultimately, the induction conditions are optimized for each using standard methods. However, for initial analysis it is possible to carry out a standardized heat shock protocol that is established for expression of other recombinant proteins in *Brassica juncea.*

FIG. 6 shows an immunoblot of transgenic *Brassica juncea* expressing human growth hormone (hGH) under control of the HSP18.2 promoter. Transgenic *Brassica juncea* were grown in potting mix. As shown in FIG. 6, a leaf weighing 1 to 3 grams fresh weight was detached from the plant and placed in a petri dish containing a filter paper moistened with water. The petri dish is covered and placed in a high humidity, 37° C. incubator for 1.5 hours. The petri dish containing the leaf was then removed from the incubator and placed for 5 hours in a 24° C. growth chamber under fluorescent lights at an intensity of 100 μmol photons $m^{-2} s^{-1}$. The plant material was then harvested and analyzed by immunoblotting using a monoclonal antibody against hGH (Sigma Chemical Co., Product #G-8523). The lower band is the 16 kDa recombinant hGH. This band is not observed before heat shock. Lane 8 shows the results from a transgenic plant transformed with the vector alone. The higher molecular weight band is a non-specific reaction with the horseradish peroxidase-linked secondary antibody used to detect immune-complexes. PA is predicted to be approximately 88 kDa and LF 93 kDa.

After an initial screen for anthrax toxin expression a more detailed analysis of expression is carried out. An ELISA method is used to quantitate the level of expression. Further analysis is carried out on subsequent plant generation. In order to avoid the need to select for transgenic plants in subsequent generations it is ultimately necessary to isolate transgenic lines that are non-segregating for the TDNA construct. This is accomplished by self-pollinating the primary transgenic plants, raising the secondary generation plants to maturity, and testing the tertiary generation for segregation of Bialophos resistance. Secondary generation individuals are identified that are non-segregating. Thereafter, progeny of non-segregating plants are bulked and used for analysis of production scale conditions (e.g., 1,600 Kg per month of dried biomass). For production scale the growth and induction conditions are optimized for plants grown as seedlings. At this point it is also desirable to characterize the insertion site and TDNA copy number of elite lines and to characterize expression at the level of mRNA expression.

Example 5

Expression of a GUS Reporter in Sprouts pBI121 containing a GUS reporter gene was transformed into *Agrobacterium tumefaciens* LBA 4404. Bacterial cultures were grown overnight in YEB medium containing 50 μg/ml kanamycin, 20 μM acetosyringone and 10 mM MES pH 5.6. Overnight cultures were centrifuged, resuspended in MMA medium (MS salts, 10 mM MES pH 5.6, 200 μM acetosyringone and 2% sucrose) at $OD_{600}$ 2.0 and used for vacuum infiltration of sprouts.

Seeds of various plants were imbibed in water for 24 hr at room temperature on a rocking platform, transferred into plastic containers with wet filter paper and incubated for 4 to 6 days (depending on plant species) under 12 hr daylight at 21° C.

Figure 8A:
FIG. 8A demonstrates staining of Mung bean sprout.
Figure 8B:
FIG. 8B demonstrates staining of Fenugreek sprouts.
Figure 9A:
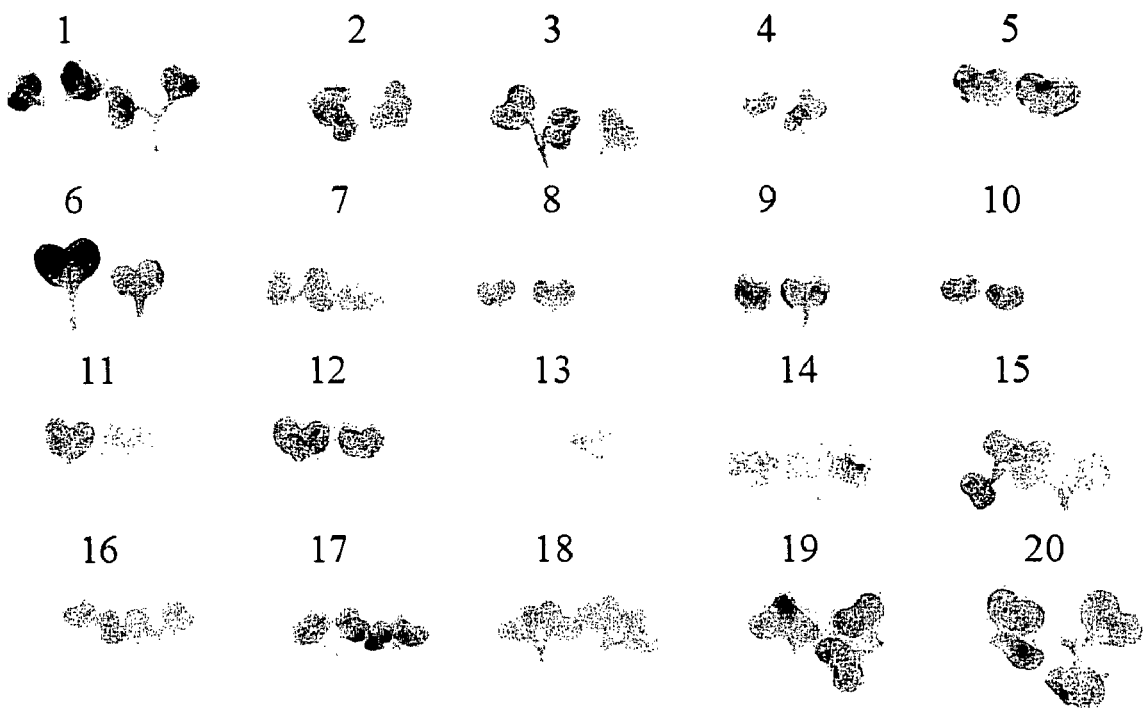
FIG. 9A demonstrates staining results.

After vacuum infiltration, sprouts were incubated for additional 48-60 hr under 12 hr daylight at 21° C. and the GUS activity was detected in situ using X-gluc histochemical substrate. The staining was performed overnight at 37° C. and the plant samples were de-stained in ethanol. The system was tested using a wide variety of sprouts. See FIGS. 8A and 8B and FIG. 9.

Example 6

Expression of Diabetes Associated Proteins and Human Growth Hormone Using Plant Virus Vector or Replicon Engineered into Agrobacterial Expression System We created a TMV-based vector in agrobacterial vector: D4-hGH or D4-GFP. For this, we first had to create multiple cloning sites in pBI121. pBI121-Xba1-BamH1-Sal1-Pac1-BsiW1-Stu1-Xho1-Spe1-Kpn1-Sac1-pBI121. Using appropriate primers and PCR, we created pBI121 with these sites. After confirming the sequence, we then proceeded to introduce TMV genomic sequence into this plasmid. See also U.S. Ser. No. 10/770,600 filed Feb. 3, 2004 and U.S. Provisional application No. 60/444,615, filed Feb. 3, 2003, incorporated herein by reference and U.S. Ser. No. 10/832,603 and U.S. provisional application 60/546,339, incorporated herein by reference, for further discussion of D4-hGH and D4-GFP. The parental vector, D4, and vectors derived therefrom, are described in Shivprasad et al., Virology, 255(2):312-23, 1999. The resultant plasmid is referred to as pBID4.

The 35S promoter of cauliflower mosaic virus was fused to TMV sequence. Thus the 35S promoter directs transcription of the TMV sequence. Upon successful incorporation into a cell, viral transcripts are produced. In certain embodiments of the invention, components needed for viral replication and spread throughout the plant are also produced. These components include, e.g., replicase, movement protein, and coat protein, which may be from TMV or from another virus such as alfalfa mosaic virus in various embodiments. These components may be encoded within the TMV sequence, the plasmid sequence, provided in a separate viral vector or plasmid, or the plant may be a transgenic plant comprising a transgene that encodes the components. See, for example U.S. Ser. No. 10/770,600 filed Feb. 3, 2004, which is incorporated herein by reference.

A subgenomic TMV promoter within the TMV sequence directs transcription of the hGH sequence. A hammerhead ribozyme was introduced 3' of the TMV sequence. The ribozyme is not required for the present invention. The nos terminator (well known in the art) is 3' of the ribozyme sequence.

Figure 10:
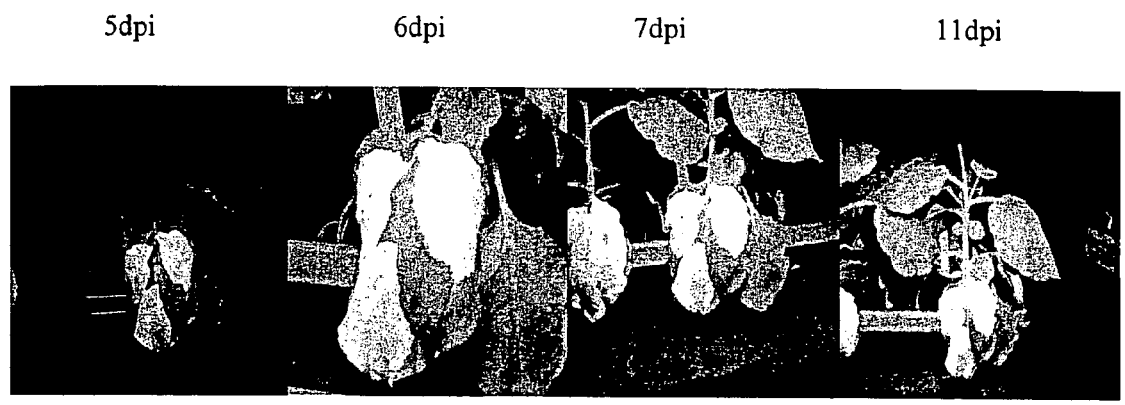
FIG. 10 demonstrates GFP expression in *N. benthamiana* over time after infiltration with pBI121/D4-GFPC3.
Figure 11:
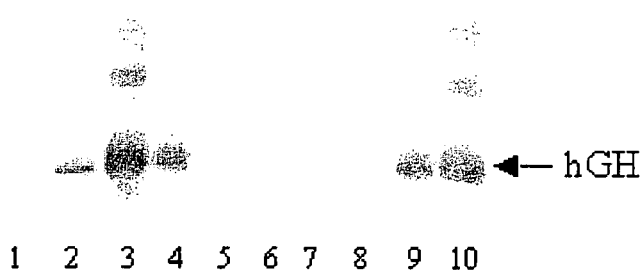
FIG. 11 demonstrates western blot analysis of hGH expression in plants as a result of infiltration with *Agrobacterium* containing a virus vector containing a sequence encoding hGH. Lanes: Lane 1: ladder; Lane 2: 50 ng hGH; Lane 3: Plant sample infiltrated with pBI121/D4-HGH 6 dpi 1:2 dilution; Lane 4: Plant sample infiltrated with pBI121/D4-HGH 6 dpi 1:10 dilution; Lane 5: Plant sample infiltrated with pBI121/D4-HGH 6 dpi 1:50 dilution; Lane 6: Plant sample infiltrated with pBI121/D4-HGH 6 dpi 1:100 dilution; Lane 7: Plant sample from Healthy plant; Lane 8: Plant sample from pBI121-infiltrate leaves; Lane 9: Plant sample from D4-HGH infected plant 13 dpi; Lane 10: Sample from D4-HGH infected clonal root line. For plant samples: one leaf disc (~5 mg tissue) is ground in 100 uL Bradley buffer with Laemmli loading buffer. 10 ul is loaded per lane. Therefore, for lanes 3-6, this primary sample was diluted.

The final vector contained D4-hGH or D4-GFP. These constructs in pBI121 were then used to transform *A. tumefaciens* and plants infiltrated with transformed *Agrobacterium*. Since a replicating virus is present we incubated the plants for 2 weeks. Leaf discs were analysed for hGH production by Western blots. GFP expression was monitored by illuminating the plants with long wave ultraviolet light and photographed. The results shown in FIG. 10 deomonstrate GFP expression throughout the infiltrated leaves. Western blot analysis shown in FIG. 11 using antibody directed to hGH confirmed that the construct was functional in plants, and hGH could be detected at high levels.

Similarly, IA-2ic was engineered into pBID4 plasmid to generate pBID4-IA-2ic. Additionally, AMV viral based vector carrying GFP was generated. Resulting plasmids was used to transform *Agrobacterium* and hydroponically grown *Nicotiana benthamiana* was infiltrated with transformed *Agrobacterium*. Briefly, *Nicotiana benthamiana* seeds were sown on a Rockwool slab (18×8×1) pre-wetted in ½ strength Hoagland solution as a nutrient in hydroponic conditions. The hydroponics plants were kept in the same solution for four weeks. Four week-old plants were then vacuum infiltrated in *Agrobacterium* suspension ($OD_{600}$ 0.1) carrying pBID4-IA-2ic or AMV viral based vector carrying GFP.

Figure 12:
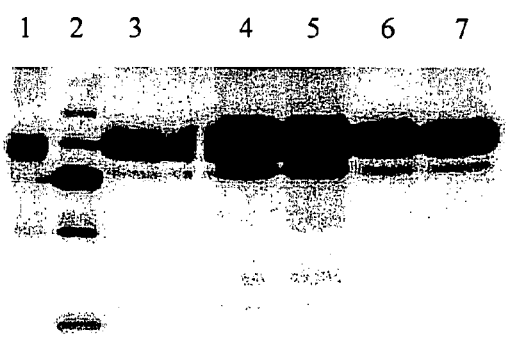
FIG. 12 demonstrates expression of IA-2ic protein in in *Nicotiana benthamiana* plants grown in hydroponics. Lanes: 1. IA-2ic standard; 2. Magic Marker; 3. Soil-grown plants injected with agrobacteria.; 4, 5. Hydroponics-grown plants 4 days after infiltration.; 6, 7. Hydroponics-grown plants 6 days after infiltration.

Bacterial cultures were grown and induced over night, then cells were re-suspended in MMA medium (MS salts, 10 mM MES pH 5.6, 20 g/l sucrose, 200 μM acetosyringone) to an $OD_{600}$ of 0.1. Re-suspended culture was incubated at room temperature for 2-3 h with gentle shaking, and hydroponics *Nicotiana benthamiana* plants were placed in the bacterial suspension, then vacuum was applied for 30-60 second at room temperature. Vacuum was quickly released to facilitate efficient infusion of the bacteria into the tissue, and infiltrated plants were kept in ½ strength Hoagland solution nutrient for 5-7 days Alternatively, the bacterial suspension was forced under the epidermis of fully-expanded leaves, using a 10 cm² syringe with no needle. Leaves were harvested between 3-6 days post-infiltration and stored at −80° C. or analyzed for expression analysis. FIG. 12 demonstrates western blot analysis of plants expressing IA-2ic. Analysis of plants infiltrated with AMV based GFP constructs under light demonstrated expression of GFP throughout leaves of infiltrated plants.

Other Embodiments

Those of ordinary skill in the art will appreciate that the foregoing represents certain preferred embodiments of the present invention and should not be construed to limit the spirit or scope of the invention as defined by the following claims.

What is claimed is:

1. A method for producing a pharmaceutically active protein in sprouted seedlings, comprising the steps of:
    infusing a sprouted seedling with Agrobacterium comprising a viral expression cassette encoding a pharmaceutically active protein and additional virus encoding proteins, wherein a viral promoter drives expression of a nucleic acid encoding the pharmaceutically active protein; and
    growing the sprouted seedling in a contained, regulatable environment;
    wherein growing the sprouted seedling allows for production of the nucleic acid encoding the pharmaceutically active protein, resulting in production of pharmaceutically active protein produced in the sprouted seedling, wherein the sprouted seedling has grown for 1-12 days post-germination prior to harvesting.

2. A method for producing a pharmaceutically active protein in sprouted seedlings, comprising the steps of:
    infusing a sprouted seedling with *Agrobacterium* comprising a viral expression cassette encoding a pharmaceutically active protein and additional virus encoding proteins, wherein a viral promoter drives expression of a nucleic acid encoding the pharmaceutically active protein; and
    growing the sprouted seedling in a contained, regulatable environment;
    wherein growing the sprouted seedling allows for production of the nucleic acid encoding the pharmaceutically active protein, resulting in production of pharmaceutically active protein produced in the sprouted seedling, wherein the sprouted seedling is harvested at the two-leaf stage.

3. The method of claim 1 or 2, further comprising the step of homogenizing live sprouted seedlings expressing the nucleic acid or protein in the presence of a homogenization buffer.

4. The method of claim 3, further comprising purifying the nucleic acid or protein from the homogenization buffer.

5. The method of claim 1 or 2, wherein the sprouted seedling is an edible sprouted seedling.

6. The method of claim 1 or 2, wherein the sprouted seedling is of the *Brassica* genus.

7. The method of claim 6, wherein the *Brassica* species is selected from the group consisting of *Brassica napus, Brassica rapa*, and *Brassica juncea*.

8. The method of claim 1 or 2, wherein the sprouted seedling is of a plant selected from the group consisting of alfalfa, radish, mustard, mung bean, broccoli, watercress, soybean, wheat, sunflower, cabbage, clover, and lentil.

9. The method of claim 1 or 2, wherein the contained, regulatable environment comprises a housing unit with climate control.

10. The method of claim 9, wherein the climate control comprises controlling any of the group selected from the temperature, the humidity, the lighting, the water delivery, the nutrient delivery, and the amount of gas delivery of the housing unit.

* * * * *

```
SEQUENCE LISTING

<160> NUMBER OF SEQ ID NOS: 2

<210> SEQ ID NO 1
<211> LENGTH: 20
<212> TYPE: DNA
<213> ORGANISM: Artificial
<220> FEATURE:
<223> OTHER INFORMATION: Brassica juncea

<400> SEQUENCE: 1
tctagaaaac aatggctaaa                                            20

<210> SEQ ID NO 2
<211> LENGTH: 15
<212> TYPE: DNA
<213> ORGANISM: Artificial
<220> FEATURE:
<223> OTHER INFORMATION: Brassica juncea

<400> SEQUENCE: 2
ataggataag agctc                                                 15
```